US007045596B2

(12) United States Patent
Umansky et al.

(10) Patent No.: US 7,045,596 B2
(45) Date of Patent: May 16, 2006

(54) FAMILY OF GENES ENCODING APOPTOSIS-RELATED PEPTIDES, PEPTIDES ENCODED THEREBY AND METHODS OF USE THEREOF

(75) Inventors: Samuil Umansky, Richmond, CA (US); Hovsep Melkonyan, Albany, CA (US)

(73) Assignee: Tanox, Inc., Houston, TX (US)

( * ) Notice: Subject to any disclaimer, the term of this patent is extended or adjusted under 35 U.S.C. 154(b) by 498 days.

(21) Appl. No.: 10/146,474

(22) Filed: May 14, 2002

(65) Prior Publication Data

US 2003/0023061 A1    Jan. 30, 2003

Related U.S. Application Data

(63) Continuation of application No. 08/937,067, filed on Sep. 24, 1997, now Pat. No. 6,433,155.

(60) Provisional application No. 60/028,363, filed on Oct. 11, 1996, provisional application No. 60/026,603, filed on Sep. 24, 1996.

(51) Int. Cl.
*C07K 14/00* (2006.01)
(52) U.S. Cl. ............... 530/350; 530/300; 536/23.1; 536/23.5; 536/26.41; 424/184.1; 424/185.1
(58) Field of Classification Search ............... 530/300, 530/350; 536/23.1, 23.5, 24.3, 26.41; 424/184.1, 424/185.1
See application file for complete search history.

(56) References Cited

U.S. PATENT DOCUMENTS

| 3,817,837 | A | 6/1974 | Rubenstein et al. ...... 195/103.5 |
|---|---|---|---|
| 3,850,752 | A | 11/1974 | Schuurs et al. ......... 195/103.5 |
| 3,939,350 | A | 2/1976 | Kronick et al. ............ 250/365 |
| 3,996,345 | A | 12/1976 | Ullman et al. ................. 424/12 |
| 4,275,149 | A | 6/1981 | Litman et al. .................. 435/7 |
| 4,277,437 | A | 7/1981 | Maggio ........................ 422/61 |
| 4,366,241 | A | 12/1982 | Tom et al. ...................... 435/7 |

FOREIGN PATENT DOCUMENTS

| WO | WO 93/04169 | 3/1993 |
|---|---|---|
| WO | WO 95/13701 | 5/1995 |
| WO | WO 95/15173 | 6/1995 |
| WO | WO 96/05232 | 2/1996 |

OTHER PUBLICATIONS

Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao, et al. The Journal of Immunology, 1989, 143(8): 2595-2601.*
Gillies et al. Human Antibodies and Hybridomas, 1990, 1(1): 47-54.*
Ameisen et al., *Immunol. Today*, 12:102-105 (1991).
Ausubel et al., eds., *Current Protocols in Molecular Biology* (1987) John Wiley & Sons, Inc.
Bates et al., *J. Cell Biol.*, 125:403-415 (1994).
Bhanot et al., *Nature*, 382:225-230 (1996).
Boudreau et al., *Science*, 267:891-893 (1995).
Chan et al., *J. Biol. Chem.*, 267:25202-25207 (1992).
Chomczynski et al., *Anal. Biochem.*, 162:156-159 (1987).
Cohen et al., *Ann. Rev. Immunol.*, 10:267-293 (1992).
Coligan et al., eds. *Current Protocols in Immunology*, (1991) John Wiley & Sons, Inc.
Cook et al., *EMBO J.*, 15:4526-4536 (1996).
Duke et al., *Lymphokine Res.*, 5:289-299 (1986).
Feinberg et al., *Analytical Biochem.*, 137:266-267 (1984).
Finch et al., *Proc. Nat'l Acad. Sci. USA*, 94:6770-6775 (1997).
Freshney, ed., *Animal Cell Culture, a practical approach*, (1987) IRL Press, Oxford, England.
Gacesa et al., *Vectors Essential Data* (1994) John Wiley & Sons Ltd., West Sussex, UK.
Gait, ed., *Oligonucleotide Synthesis, a practical approach* (1984) IRL Press, Oxford, England.
Gavin et al., *Genes and Development*, 4:2319-2332 (1990).
Gerschenson et al., *FASEB J.* 6:2450-2455 (1992).
Hannum et al., *T. Biochem. Sci.*, 20:73-77 (1995).
Harlow et al., *Antibodies. A laboratory Manual*, (1988) Cold Spring Harbor Laboratory, Cold Spring Harbor, New York.
Hillier et al., Accession No. AA024771 (1996).
Hillier et al., Accession No. H16121 (1995).
Hillier et al., Accession No. H14917 (1995).
Hillier et al., "The Washington University Merck EST project, AC H87071," (Nov. 22, 1995), Heidelberg, XP002054775, 2 pages total.
Hillier et al., "The Washington University Merck EST project, AC H45312," (Nov. 18, 1995), Heidelberg, XP002057808, 1 page total.
Hoang et al., *J. Biol. Chem.*, 271:26131-26137 (1996).
Hockenberry et al., *Cell*, 75:241-251 (1993).
Hu et al., *Biochem. Biophys. Res. Comm.*, 247:287-293 (1998).

(Continued)

*Primary Examiner*—Susan Ungar
*Assistant Examiner*—Minh-Tam Davis
(74) *Attorney, Agent, or Firm*—Sheridan Ross P.C.

(57) ABSTRACT

An isolated polynucleotide at least 60% homologous to SEQ ID NO: 1, 3, 5 or 18 encoding a SARP polypeptide; vectors comprising a polynucleotide sequence encoding at least 11 consecutive amino acids of αSARP polypeptide; a host cell transformed with an isolated polynucleotide or vector; antibodies specific for SARP and use of such polynucleotides and antibodies in diagnostic and therapeutic method. Therapeutic uses of antibodies and polynucleotides of sarp. Methods for treating diseases related to the regulation of SARP expression in tissue and bodily fluid samples, including cancers.

7 Claims, 15 Drawing Sheets

OTHER PUBLICATIONS

Kanter et al., *Biochem. Biophys. Res. Comm.*, 118:392-399 (1984).
Kiefer et al., *Biochem. Biophys. Res. Comm.*, 176:219:225 (1991).
Kolesnick et al., *J. Esp. Med.*, 181:1949-1952 (1995).
Korinek et al., *Science*, 275:1784-1792 (1997).
Kozopas et al., *Proc. Natl. Acad. Sci. USA*, 90:3516-3520 (1993).
Kruman et al., *J. Cell. Physicol.*, 148:267-273 (1991).
Leyns et al., *Cell*, 88:747-756 (1997).
Lichtenstein et al., *Anal. Biochem.*, 207:280-284 (1992).
Marra et al., The Washington University HHMI Mouse EST Project, AC W58777 (Jun. 9, 1996), Heidelberg, XP002057807, 2 pages total.
Melkonyan et al., *Proc. Natl. Acad. Sci. USA*, 94:13636-13641 (1997).
Melkonyan, "A new family of secreted apoptosis-related proteins" (Abstract from Conference on Cell Cycle Control & Apoptosis: Basic Mechanisms & Novel Therapies, Jun. 30-Jul. 1, 1997, London, UK).
Melkonyan, "A new family of apoptosis-related genes" (Abstract from Conference on Apoptosis-Practical Applications and Novel Therapies, Nov. 20-21, 1997, Boston, MA).
*Methods in Enzymology* Academic Press, Inc.
Miller et al., eds. *Gene Transfer Vectors for Mammalian Cells* (1987). Cold Spring Harbor Laboratory, Cold Spring Harbor, New York.
Morin et al., *Science*, 275:1787-1790 (1997).
Mullis et al., eds., *The Polymerase Chain Reaction* (1994).
Nonradioactive in Situ Hybridization Application Manual Second Edition, 1996, p. 127.
Nusse et al., *Cell*, 69:1073-1087 (1992).
Orsulic et al., *Curr. Biol.*, 6:1363-1367 (1996).
Pai et al., *Development*, 124:2255-2266 (1997).
Rattner et al., *Proc. Natl. Acad. Sci. USA*, 94:2859-2863 (1997).
Perrimon, *Cell*, 86:513-516 (1996).
Ruoslahti et al., *Cell*, 77:477-478 (1994).
Rubinfeld et al., *Science*, 272:1023-1026 (1996).
Sambrook et al., *Molecular Cloning: A Laboratory Manual 2d Ed.*, (1989) Cold Spring Harbor Laboratory Press, New York.
Sheppard et al., *J. AIDS*, 5:143-147 (1992).
Shirozu et al., *Genomics*, 37:273-280 (1996).
Siegfried et a l., *Nature*, 367:76-79 (1994).
Thompson, *Science*, 267:1456-1462 (1995).
Tomei et al., "Apoptosis: The molecular basis of cell death" *Curr. Comm. Cell Mol. Biol.* (1991).
Tomei and Cope et al. eds., "Apoptosis II:The Molecular basis of apoptosis in disease" *Current Communications in Molecular Biology 8*, Cold Springs Harbor Laboratory Press, New York (1994).
Tomei et al., *Proc. Natl. Acad. USA*, 90:853-857 (1993).
Tomei et al., *Biochem. Biophys. Res. Comm.*, 155:324-331 (1988).
Tsujimoto et al., *Science*, 226:1097-1099 (1984).
Wang et al., *J. Biol. Chem.*, 271:4468-4476 (1995).
Weir et al., eds. *Handbook of Experimental Immunology*, (1986) Alden Press, Oxford, Great Britain.
Wyllie, *Nature*, 284:555-556 (1980).
Yang-Snyder et al., *Curr. Biol.*, 6:1302-1306 (1996).
Yost et al., *Genes and Development*, 10:1443-1454 (1996).
Yuan et al., *Develop. Biol.*, 138:33-41 (1990).
Zapf et al., *J. Biol. Chem.*, 265:14892-14898 (1990).
Zyad et al., *Cancer Res.*, 54:825-831 (1994).

\* cited by examiner

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
        (A) LENGTH: 2030 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 253..1137

(xi) SEQUENCE DESCRIPTION: SEQ ID NO: 1:

```
AATTCGGAGA TCTACAGGCC TGTAGATCTC CGGCTCACTC TGCTCCCCCG GGTCGGAGCC      60

CCCCGGAGCT GCGCGCGGGC TTGCAGTGCC TTGCCCGCGC CGACCTCCCG GCGCCCGGCT     120

TCGCGCGTTC GGCCGCCCGC TGTCCAGAGC CCCCACGAGC AGAGCGAGGG AGTCCCGGAC     180

GAGCTCGAGC TCCGGCCGCC TCTCGCTTCC CCCGCTCGGC TCCCTCCGCC CCCCGGGGGT     240

CGCTAGTCCA CG ATG CCG CGG GGC CCT GCC TCG CTG CTG CTG CTA GTC        288
              Met Pro Arg Gly Pro Ala Ser Leu Leu Leu Leu Val
                1               5                  10

CTC GCC TCG CAC TGC TGC CTG GGC TCG GCG CGT GGG CTC TTC CTC TTC       336
Leu Ala Ser His Cys Cys Leu Gly Ser Ala Arg Gly Leu Phe Leu Phe
           15                  20                  25

GGC CAG CCC GAC TTC TCC TAC AAG CGC ACG AAC TGC AAG CCC ATC CCC       384
Gly Gln Pro Asp Phe Ser Tyr Lys Arg Thr Asn Cys Lys Pro Ile Pro
    30                  35                  40

GCC AAC CTG CAG CTG TGC CAC GGC ATC GAG TAC CAG AAC ATG CGG CTG       432
Ala Asn Leu Gln Leu Cys His Gly Ile Glu Tyr Gln Asn Met Arg Leu
45                  50                  55                  60

CCC AAC CTG CTG GGC CAC GAG ACC ATG AAG GAG GTG CTG GAG CAG GCG       480
Pro Asn Leu Leu Gly His Glu Thr Met Lys Glu Val Leu Glu Gln Ala
                65                  70                  75

GGC GCC TGG ATT CCG CTG GTC ATG AAG CAG TGC CAC CCG GAC ACC AAG       528
Gly Ala Trp Ile Pro Leu Val Met Lys Gln Cys His Pro Asp Thr Lys
            80                  85                  90

AAG TTC CTG TGC TCG CTC TTC GCC CCT GTC TGT CTC GAC GAC CTA GAT       576
Lys Phe Leu Cys Ser Leu Phe Ala Pro Val Cys Leu Asp Asp Leu Asp
        95                  100                 105

GAG ACC ATC CAG CCG TGT CAC TCG CTC TGC GTG CAG GTG AAG GAC CGC       624
Glu Thr Ile Gln Pro Cys His Ser Leu Cys Val Gln Val Lys Asp Arg
```

```
              110                 115                 120
TGC GCC CCG GTC ATG TCC GCC TTC GGC TTC CCC TGG CCA GAC ATG CTG        672
Cys Ala Pro Val Met Ser Ala Phe Gly Phe Pro Trp Pro Asp Met Leu
125                 130                 135                 140

GAG TGC GAC CGT TTC CCG CAG GAC AAC GAC CTC TGC ATC CCC CTC GCT        720
Glu Cys Asp Arg Phe Pro Gln Asp Asn Asp Leu Cys Ile Pro Leu Ala
                145                 150                 155

AGT AGC GAC CAC CTC CTG CCG GCC ACA GAG GAA GCT CCC AAG GTG TGT        768
Ser Ser Asp His Leu Leu Pro Ala Thr Glu Glu Ala Pro Lys Val Cys
            160                 165                 170

GAA GCC TGC AAA ACC AAG AAT GAG GAC GAC AAC GAC ATC ATG GAA ACC        816
Glu Ala Cys Lys Thr Lys Asn Glu Asp Asp Asn Asp Ile Met Glu Thr
        175                 180                 185

CTT TGT AAA AAT GAC TTC GCA CTG AAA ATC AAA GTG AAG GAG ATA ACG        864
Leu Cys Lys Asn Asp Phe Ala Leu Lys Ile Lys Val Lys Glu Ile Thr
    190                 195                 200

TAC ATC AAC AGA GAC ACC AAG ATC ATC CTG GAG ACA AAG AGC AAG ACC        912
Tyr Ile Asn Arg Asp Thr Lys Ile Ile Leu Glu Thr Lys Ser Lys Thr
205                 210                 215                 220

ATT TAC AAG CTG AAC GGC GTG TCC GAA AGG GAC CTG AAG AAA TCC GTG        960
Ile Tyr Lys Leu Asn Gly Val Ser Glu Arg Asp Leu Lys Lys Ser Val
                225                 230                 235

CTG TGG CTC AAA GAC AGC CTG CAG TGC ACC TGT GAG GAG ATG AAC GAC       1008
Leu Trp Leu Lys Asp Ser Leu Gln Cys Thr Cys Glu Glu Met Asn Asp
            240                 245                 250

ATC AAC GCT CCG TAT CTG GTC ATG GGA CAG AAG CAG GGC GGC GAA CTG       1056
Ile Asn Ala Pro Tyr Leu Val Met Gly Gln Lys Gln Gly Gly Glu Leu
        255                 260                 265

GTG ATC ACC TCC GTG AAA CGG TGG CAG AAG GGC CAG AGA GAG TTC AAG       1104
Val Ile Thr Ser Val Lys Arg Trp Gln Lys Gly Gln Arg Glu Phe Lys
    270                 275                 280

CGC ATC TCC CGC AGC ATC CGC AAG CTG CAA TGC TAGTTTCCCA GTGGGGTGGC     1157
Arg Ile Ser Arg Ser Ile Arg Lys Leu Gln Cys
285                 290                 295

TTCTCTCCAT CCAGGCCCTG AGCTCTGTAG ACCACTTGCC TCCGGACCTC ATTTCCGGTT     1217

TCCCAAGCAC AGTCCGGGAA AGCTACAGCC CCAGCTTGGA GCCGCTTGCC CTGCCTCCTG     1277

CATGTGTGTA TCCCTAACAT GTCCTGAGTT ATAAGGCCCT AGGAGGCCTT GGAAACCCAT     1337

AGCTGTTTTC ACGGAAAGCG AAAAGCCCAT CCAGATCTTG TACAAATATT CAAACTAATA     1397

AAATCATGAC TATTTTTATG AAGTTTTAGA ACAGCTCGTT TTAAGGTTAG TTTTGAATAG     1457

CTGTAGTACT TTGACCCGAG GGGCATTTTC TCTCTTTGGT CAGTCTGTTG GCTTATACCG     1517

TGCACTTAGG TTGCCATGTC AGGCGAATTG TTTCTTTTTT TTTTTTTTTT TCCCTCTGTG     1577

GTCTAAGCTT GTGGGTCCCA GACTTAGTTG AGATAAAGCT GGCTGTTATC TCAAAGTCTT     1637

CCTCAGTTCC AGCCTGAGAA TCGGCATCTA AGTCTTCAAA CATTTCGTTG CTCGTTTTAT     1697

GCCCTCATGA GCTCTGACCA TTGCATGCGT TCCCATCCCA GCTACAGAAC TTCAGTTTAT     1757

AAGCACACAG TAACCATTCC TCATTGCATG ATGCCCTCAA ATAAAAGTG AATACAGTCT      1817

ATAAATTGAC GAGTATTTTA AGCTTTGTTT AAAACATCTT TTAATTCAAT TTTTTAATCA     1877

TTTTTTTTGC AAACTAAATC ATTGTAGCTT ACCTGTAATA TACGTAGTAG TTGACCTGGA     1937

AAAGTTGTAA AAATATTGCT TTAACCGACA CTGTAAATAT TTCAGATAAA CATTATATTC     1997

TTTGTATATA AACTCCTGTA GATCTCCGAA TTC                                  2030
```

(2) INFORMATION FOR SEQ ID NO: 2:

(i) SEQUENCE CHARACTERISTICS:
      (A) LENGTH: 295 amino acids
      (B) TYPE: amino acid
      (D) TOPOLOGY: linear (ii) MOLECULE TYPE: protein (xi) SEQUENCE DESCRIPTION: SEQ ID NO: 2:

```
Met Pro Arg Gly Pro Ala Ser Leu Leu Leu Val Leu Ala Ser His
 1               5                  10                  15

Cys Cys Leu Gly Ser Ala Arg Gly Leu Phe Leu Phe Gly Gln Pro Asp
                20                  25                  30

Phe Ser Tyr Lys Arg Thr Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
 65                 70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
                100                 105                 110

Pro Cys His Ser Leu Cys Val Gln Val Lys Asp Arg Cys Ala Pro Val
            115                 120                 125

Met Ser Ala Phe Gly Phe Pro Trp Pro Asp Met Leu Glu Cys Asp Arg
130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Thr Lys Asn Glu Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
    290                 295
```

(2) INFORMATION FOR SEQ ID NO: 3:

(i) SEQUENCE CHARACTERISTICS:
      (A) LENGTH: 870 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS (B) LOCATION: 235..870

(xi) SEQUENCE DESCRIPTION: SEQ ID NO: 3:

```
GGCTCATTCT GCTCCCCCGG GTCGGAGCCC CCCGGAGCTG CGCGCGGGCT TGCAGCGCCT        60

CGCCCGCGCT GTCCTCCCGG TGTCCCGCTT CTCCGCGCCC CAGCCGCCGG CTGCCAGCTT       120

TTCGGGGCCC CGAGTCGCAC CCAGCGAAGA GAGCGGGCCC GGGACAAGCT CGAACTCCGG       180

CCGCCTCGCC CTTAACCAGC TCCGTCCCTC TACCCCCTAG GGGTCGCGCC CACG ATG        237
                                                             Met
```

| | | | | | | | | | | | | | | | | |
|---|---|---|---|---|---|---|---|---|---|---|---|---|---|---|---|---|
| CTG | CAG | GGC | CCT | GGC | TCG | CTG | CTG | CTG | CTC | TTC | CTC | GCC | TCG | CAC | TGC | 285 |
| Leu | Gln | Gly | Pro | Gly | Ser | Leu | Leu | Leu | Leu | Phe | Leu | Ala | Ser | His | Cys | |
| | | | 300 | | | | | 305 | | | | | 310 | | | |
| TGC | CTG | GGC | TCG | GCG | CGC | GGG | CTC | TTC | CTC | TTT | GGC | CAG | CCC | GAC | TTC | 333 |
| Cys | Leu | Gly | Ser | Ala | Arg | Gly | Leu | Phe | Leu | Phe | Gly | Gln | Pro | Asp | Phe | |
| | | | | 315 | | | | | 320 | | | | | 325 | | |
| TCC | TAC | AAG | CGC | AGC | AAT | TGC | AAG | CCC | ATC | CCG | GCC | AAC | CTG | CAG | CTG | 381 |
| Ser | Tyr | Lys | Arg | Ser | Asn | Cys | Lys | Pro | Ile | Pro | Ala | Asn | Leu | Gln | Leu | |
| | | | | 330 | | | | | 335 | | | | | 340 | | |
| TGC | CAC | GGC | ATC | GAA | TAC | CAG | AAC | ATG | CGG | CTG | CCC | AAC | CTG | CTG | GGC | 429 |
| Cys | His | Gly | Ile | Glu | Tyr | Gln | Asn | Met | Arg | Leu | Pro | Asn | Leu | Leu | Gly | |
| 345 | | | | | 350 | | | | | 355 | | | | | 360 | |
| CAC | GAG | ACC | ATG | AAG | GAG | GTG | CTG | GAG | CAG | GCC | GGC | GCT | TGG | ATC | CCG | 477 |
| His | Glu | Thr | Met | Lys | Glu | Val | Leu | Glu | Gln | Ala | Gly | Ala | Trp | Ile | Pro | |
| | | | | 365 | | | | | 370 | | | | | 375 | | |
| CTG | GTC | ATG | AAG | CAG | TGC | CAC | CCG | GAC | ACC | AAG | AAG | TTC | CTG | TGC | TCG | 525 |
| Leu | Val | Met | Lys | Gln | Cys | His | Pro | Asp | Thr | Lys | Lys | Phe | Leu | Cys | Ser | |
| | | | | 380 | | | | | 385 | | | | | 390 | | |
| CTC | TTC | GCC | CCC | GTC | TGC | CTC | GAT | GAC | CTA | GAC | GAG | ACC | ATC | CAG | CCA | 573 |
| Leu | Phe | Ala | Pro | Val | Cys | Leu | Asp | Asp | Leu | Asp | Glu | Thr | Ile | Gln | Pro | |
| | | | | 395 | | | | | 400 | | | | | 405 | | |
| TGC | CAC | TCT | CGN | TGC | GTG | CAG | GTG | AAG | GAT | CGC | TGC | GCC | CCG | GTC | ATG | 621 |
| Cys | His | Ser | Xaa | Cys | Val | Gln | Val | Lys | Asp | Arg | Cys | Ala | Pro | Val | Met | |
| | | | 410 | | | | | 415 | | | | | 420 | | | |
| TCC | GCC | TTC | GGC | TTC | CCC | TGG | CCC | GAC | ATG | CTT | GAG | TGC | GAC | CGT | TTC | 669 |
| Ser | Ala | Phe | Gly | Phe | Pro | Trp | Pro | Asp | Met | Leu | Glu | Cys | Asp | Arg | Phe | |
| 425 | | | | | 430 | | | | | 435 | | | | | 440 | |
| CCC | CAG | GAC | AAC | GAC | CTT | TGC | ATC | CCC | CTC | GCT | AGC | AGC | GAC | CAC | CTC | 717 |
| Pro | Gln | Asp | Asn | Asp | Leu | Cys | Ile | Pro | Leu | Ala | Ser | Ser | Asp | His | Leu | |
| | | | | 445 | | | | | 450 | | | | | 455 | | |
| CTG | CCA | GCC | ACC | GAG | GAA | GCT | CCA | AAG | GTA | TGT | GAA | GCC | TGC | AAA | AAT | 765 |
| Leu | Pro | Ala | Thr | Glu | Glu | Ala | Pro | Lys | Val | Cys | Glu | Ala | Cys | Lys | Asn | |
| | | | 460 | | | | | 465 | | | | | 470 | | | |
| AAA | AAT | GAT | GAT | GAC | AAC | GAC | ATA | ATG | GAA | ACG | CTT | TGT | AAA | AAT | GAT | 813 |
| Lys | Asn | Asp | Asp | Asp | Asn | Asp | Ile | Met | Glu | Thr | Leu | Cys | Lys | Asn | Asp | |
| | | | 475 | | | | | 480 | | | | | 485 | | | |
| TTT | GCA | CTG | AAA | ATA | AAA | GTG | AAG | GAG | ATA | ACC | TAC | ATC | AAC | CGT | CGA | 861 |
| Phe | Ala | Leu | Lys | Ile | Lys | Val | Lys | Glu | Ile | Thr | Tyr | Ile | Asn | Arg | Arg | |
| | | 490 | | | | | 495 | | | | | 500 | | | | |
| CGC | GGC | CGC | | | | | | | | | | | | | | 870 |
| Arg | Gly | Arg | | | | | | | | | | | | | | |
| 505 | | | | | | | | | | | | | | | | |

(2) INFORMATION FOR SEQ ID NO: 4:

(i) SEQUENCE CHARACTERISTICS:
        (A) LENGTH: 212 amino acids
        (B) TYPE: amino acid
        (D) TOPOLOGY: linear (ii) MOLECULE TYPE: protein -continued (xi) SEQUENCE DESCRIPTION: SEQ ID NO: 4:

```
Met Leu Gln Gly Pro Gly Ser Leu Leu Leu Phe Leu Ala Ser His
 1               5                  10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Xaa Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Arg Arg Gly Arg
    210
```

(2) INFORMATION FOR SEQ ID NO: 5:

(i) SEQUENCE CHARACTERISTICS:
        (A) LENGTH: 1984 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 216..1166

(xi) SEQUENCE DESCRIPTION: SEQ ID NO: 5:

```
AAGCTTGATA TCGAATTCGC GGCCGCGTCG ACGGGAGGCG CCAGGATCAG TCGGGGCACC        60

CGCAGCGCAG GCTGCCACCC ACCTGGGCGA CCTCCGCGGC GGCGGCGGCG GCGGCTGGGT       120

AGAGTCAGGG CCGGGGGCGC ACGCCGGAAC ACCTGGGCCG CCGGGCACCG AGCGTCGGGG       180

GGCTGCGCGG CGCGACCCTG GAGAGGGCGC AGCCG ATG CGG GCG GCG GCG GCG         233
                                       Met Arg Ala Ala Ala Ala
                                           215

GCG GGG GGC GTG CGG ACG GCC GCG CTG GCG CTG CTG CTG GGG GCG CTG         281
Ala Gly Gly Val Arg Thr Ala Ala Leu Ala Leu Leu Leu Gly Ala Leu
    220                 225                 230

CAC TGG GCG CCG GCG CGC TGC GAG GAG TAC GAC TAC TAT GGC TGG CAG         329
His Trp Ala Pro Ala Arg Cys Glu Glu Tyr Asp Tyr Tyr Gly Trp Gln
```

-continued

```
                235                 240                 245                 250
GCC GAG CCG CTG CAC GGC CGC TCC TAC TCC AAG CCG CCG CAG TGC CTT         377
Ala Glu Pro Leu His Gly Arg Ser Tyr Ser Lys Pro Pro Gln Cys Leu
                    255                 260                 265

GAC ATC CCT GCC GAC CTG CCG CTC TGC CAC ACG GTG GGC TAC AAG CGC         425
Asp Ile Pro Ala Asp Leu Pro Leu Cys His Thr Val Gly Tyr Lys Arg
                270                 275                 280

ATG CGG CTG CCC AAC CTG CTG GAG CAC GAG AGC CTG GCC GAA GTG AAG         473
Met Arg Leu Pro Asn Leu Leu Glu His Glu Ser Leu Ala Glu Val Lys
                    285                 290                 295

CAG CAG GCG AGC AGC TGG CTG CCG CTG CTG GCC AAG CGC TGC CAC TCG         521
Gln Gln Ala Ser Ser Trp Leu Pro Leu Leu Ala Lys Arg Cys His Ser
                300                 305                 310

GAT ACG CAG GTC TTC CTG TGC TCG CTC TTT GCG CCC GTC TGT CTC GAC         569
Asp Thr Gln Val Phe Leu Cys Ser Leu Phe Ala Pro Val Cys Leu Asp
315                 320                 325                 330

CGG CCC ATC TAC CCG TGC CGC TCG CTG TGC GAG GCC GTG CGC GCC GGC         617
Arg Pro Ile Tyr Pro Cys Arg Ser Leu Cys Glu Ala Val Arg Ala Gly
                    335                 340                 345

TGC GCG CCG CTC ATG GAG GCC TAC GGC TTC CCC TGG CCT GAG ATG CTG         665
Cys Ala Pro Leu Met Glu Ala Tyr Gly Phe Pro Trp Pro Glu Met Leu
                350                 355                 360

CAC TGC CAC AAG TTC CCC CTG GAC AAC GAC CTC TGC ATC GCC GTG CAG         713
His Cys His Lys Phe Pro Leu Asp Asn Asp Leu Cys Ile Ala Val Gln
                    365                 370                 375

TTC GGG CAC CTG CCC GCC ACC GCG CCT CCA GTG ACC AAG ATC TGC GCC         761
Phe Gly His Leu Pro Ala Thr Ala Pro Pro Val Thr Lys Ile Cys Ala
                380                 385                 390

CAG TGT GAG ATG GAG CAC AGT GCT GAC GGC CTC ATG GAG CAG ATG TGC         809
Gln Cys Glu Met Glu His Ser Ala Asp Gly Leu Met Glu Gln Met Cys
395                 400                 405                 410

TCC AGT GAC TTT GTG GTC AAA ATG CGC ATC AAG GAG ATC AAG ATA GAG         857
Ser Ser Asp Phe Val Val Lys Met Arg Ile Lys Glu Ile Lys Ile Glu
                    415                 420                 425

AAT GGG GAC CGG AAG CTG ATT GGA GCC CAG AAA AAG AAG AAG CTG CTC         905
Asn Gly Asp Arg Lys Leu Ile Gly Ala Gln Lys Lys Lys Lys Leu Leu
                430                 435                 440

AAG CCG GGC CCC CTG AAG CGC AAG GAC ACC AAG CGG CTG GTG CTG CAC         953
Lys Pro Gly Pro Leu Lys Arg Lys Asp Thr Lys Arg Leu Val Leu His
                    445                 450                 455

ATG AAG AAT GGC GCG GGC TGC CCC TGC CCA CAG CTG GAC AGC CTG GCG        1001
Met Lys Asn Gly Ala Gly Cys Pro Cys Pro Gln Leu Asp Ser Leu Ala
                460                 465                 470

GGC AGC TTC CTG GTC ATG GGC CGC AAA GTG GAT GGA CAG CTG CTG CTC        1049
Gly Ser Phe Leu Val Met Gly Arg Lys Val Asp Gly Gln Leu Leu Leu
475                 480                 485                 490

ATG GCC GTC TAC CGC TGG GAC AAG AAG AAT AAG GAG ATG AAG TTT GCA        1097
Met Ala Val Tyr Arg Trp Asp Lys Lys Asn Lys Glu Met Lys Phe Ala
                    495                 500                 505

GTC AAA TTC ATG TTC TCC TAC CCC TGC TCC CTC TAC TAC CCT TTC TTC        1145
Val Lys Phe Met Phe Ser Tyr Pro Cys Ser Leu Tyr Tyr Pro Phe Phe
                510                 515                 520

TAC GGG GCG GCA GAG CCC CAC TGAAGGGCAC TCCTCCTTGC CCTGCCAGCT           1196
Tyr Gly Ala Ala Glu Pro His
                525

GTGCCTTGCT TGCCCTCTGG CCCCGCCCCA ACTTCCAGGC TGACCCGGCC CTACTGGAGG      1256

GTGTTTTCAC GAATGTTGTT ACTGGCACAA GGCCTAAGGG ATGGGCACGG AGCCCAGGCT      1316

GTCCTTTTTG ACCCAGGGGT CCTGGGGTCC CTGGGATGTT GGGCTTCCTC TCTCAGGAGC      1376
```

```
AGGGCTTCTT CATCTGGGTG AAGACCTCAG GGTCTCAGAA AGTAGGCAGG GGAGGAGAGG    1436

GTAAGGGAAA GGTGGAGGGG CTCAGGGCAC CCTGAGGCGG AGGTTTCAGA GTAGAAGGTG    1496

ATGTCAGCTC CAGCTCCCCT CTGTCGGTGG TGGGGCCTCA CCTTGAAGAG GGAAGTCTCA    1556

ATATTAGGCT AAGCTATTTG GGAAAGTTCT CCCCACCGCC CCTGTACGCG TCATCCTAGC    1616

CCCCCTTAGG AAAGGAGTTA GGGTCTCAGT GCCTCCAGCC ACACCCCTG CCTTCCCCAG     1676

CTTGCCCATT TCCCTGCCCC AAGGCCCAGA GCTCCCCCCA GACTGGAGAG CAAGCCCAGC    1736

CCAGCCTCGG CATAGACCCC CTTCTGGTCC GCCCGTGGCT CGATTCCCGG GATTCATTCC    1796

TCAGCCTCTG CTTCTCCCTT TTATCCCAAT AAGTTATTGC TACTGCTGTG AGGCCATAGG    1856

TACTAGACAA CCAATACATG CAGGGTTGGG TTTTCTAATT TTTTTAACTT TTTAATTAAA    1916

TCAAAGGTCG ACGCGCGGCC GCGGAATTCC TGCAGCCCGG GGGATCCCCG GGTACCGAGC    1976

TCGAATTC                                                             1984
```

(2) INFORMATION FOR SEQ ID NO: 6:

(i) SEQUENCE CHARACTERISTICS:
       (A) LENGTH: 317 amino acids
       (B) TYPE: amino acid
       (D) TOPOLOGY: linear (ii) MOLECULE TYPE: protein (xi) SEQUENCE DESCRIPTION: SEQ ID NO: 6:

```
Met Arg Ala Ala Ala Ala Gly Gly Val Arg Thr Ala Ala Leu Ala
 1               5                  10                  15

Leu Leu Leu Gly Ala Leu His Trp Ala Pro Ala Arg Cys Glu Glu Tyr
                20                  25                  30

Asp Tyr Tyr Gly Trp Gln Ala Glu Pro Leu His Gly Arg Ser Tyr Ser
            35                  40                  45

Lys Pro Pro Gln Cys Leu Asp Ile Pro Ala Asp Leu Pro Leu Cys His
50                  55                  60

Thr Val Gly Tyr Lys Arg Met Arg Leu Pro Asn Leu Leu Glu His Glu
65                  70                  75                  80

Ser Leu Ala Glu Val Lys Gln Gln Ala Ser Ser Trp Leu Pro Leu Leu
                85                  90                  95

Ala Lys Arg Cys His Ser Asp Thr Gln Val Phe Leu Cys Ser Leu Phe
                100                 105                 110

Ala Pro Val Cys Leu Asp Arg Pro Ile Tyr Pro Cys Arg Ser Leu Cys
                115                 120                 125

Glu Ala Val Arg Ala Gly Cys Ala Pro Leu Met Glu Ala Tyr Gly Phe
130                 135                 140

Pro Trp Pro Glu Met Leu His Cys His Lys Phe Pro Leu Asp Asn Asp
145                 150                 155                 160

Leu Cys Ile Ala Val Gln Phe Gly His Leu Pro Ala Thr Ala Pro Pro
                165                 170                 175

Val Thr Lys Ile Cys Ala Gln Cys Glu Met Glu His Ser Ala Asp Gly
                180                 185                 190

Leu Met Glu Gln Met Cys Ser Ser Asp Phe Val Val Lys Met Arg Ile
            195                 200                 205

Lys Glu Ile Lys Ile Glu Asn Gly Asp Arg Lys Leu Ile Gly Ala Gln
            210                 215                 220

Lys Lys Lys Lys Leu Leu Lys Pro Gly Pro Leu Lys Arg Lys Asp Thr
225                 230                 235                 240
```

```
Lys Arg Leu Val Leu His Met Lys Asn Gly Ala Gly Cys Pro Cys Pro
                245                 250                 255

Gln Leu Asp Ser Leu Ala Gly Ser Phe Leu Val Met Gly Arg Lys Val
            260                 265                 270

Asp Gly Gln Leu Leu Met Ala Val Tyr Arg Trp Asp Lys Lys Asn
        275                 280                 285

Lys Glu Met Lys Phe Ala Val Lys Phe Met Phe Ser Tyr Pro Cys Ser
    290                 295                 300

Leu Tyr Tyr Pro Phe Phe Tyr Gly Ala Ala Glu Pro His
305                 310                 315

(2) INFORMATION FOR SEQ ID NO: 7:

(i) SEQUENCE CHARACTERISTICS:
        (A) LENGTH: 314 amino acids
        (B) TYPE: amino acid
        (C) STRANDEDNESS: single
        (D) TOPOLOGY: linear (xi) SEQUENCE DESCRIPTION: SEQ ID NO: 7:

Met Gly Ile Gly Arg Ser Glu Gly Gly Arg Gly Ala Ala Leu Gly
1               5                   10                  15

Val Leu Leu Ala Leu Gly Ala Ala Leu Leu Ala Val Gly Ser Ala Ser
            20                  25                  30

Glu Tyr Asp Tyr Val Ser Phe Gln Ser Asp Ile Gly Pro Tyr Gln Ser
        35                  40                  45

Gly Arg Phe Tyr Thr Lys Pro Pro Gln Cys Val Asp Ile Pro Ala Asp
    50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Ala Gly Thr Gln Val Phe
            100                 105                 110

Leu Cys Ser Leu Phe Ala Pro Val Cys Leu Asp Arg Pro Ile Tyr Pro
        115                 120                 125

Cys Arg Trp Leu Cys Glu Ala Val Arg Asp Ser Cys Glu Pro Val Met
    130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Pro Thr Glu
                165                 170                 175

Ala Ser Lys Pro Gln Gly Thr Thr Val Cys Pro Pro Cys Asp Asn Glu
            180                 185                 190

Leu Lys Ser Glu Ala Ile Ile Glu His Leu Cys Ala Ser Glu Phe Ala
        195                 200                 205

Leu Arg Met Lys Ile Lys Glu Val Lys Lys Glu Asn Gly Asp Lys Lys
    210                 215                 220

Ile Val Pro Lys Lys Lys Lys Pro Leu Lys Leu Gly Pro Ile Lys Lys
225                 230                 235                 240

Lys Asp Leu Lys Lys Leu Val Leu Tyr Leu Lys Asn Gly Ala Asp Cys
                245                 250                 255

Pro Cys His Gln Leu Asp Asn Leu Ser His His Phe Leu Ile Met Gly
            260                 265                 270

Arg Lys Val Lys Ser Gln Tyr Leu Leu Thr Ala Ile His Lys Trp Asp
```

```
                275                 280                 285
Lys Lys Asn Lys Glu Phe Lys Asn Phe Met Lys Met Lys Asn His
    290                 295                 300
Glu Cys Pro Thr Phe Gln Ser Val Phe Lys
305                 310
```

(2) INFORMATION FOR SEQ ID NO: 8:

(i) SEQUENCE CHARACTERISTICS:
        (A) LENGTH: 565 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Met Arg Pro Arg Ser Ala Leu Pro Arg Leu Leu Leu Pro Leu Leu Leu
1               5                   10                  15
Leu Pro Ala Ala Gly Pro Ala Gln Phe His Gly Glu Lys Gly Ile Ser
                20                  25                  30
Ile Pro Asp His Gly Phe Cys Gln Pro Ile Ser Ile Pro Leu Cys Thr
                35                  40                  45
Asp Ile Ala Tyr Asn Gln Thr Ile Met Pro Asn Leu Leu Gly His Thr
50                  55                  60
Asn Gln Glu Asp Ala Gly Leu Glu Val His Gln Phe Tyr Pro Leu Val
65                  70                  75                  80
Lys Val Gln Cys Ser Pro Glu Leu Arg Phe Phe Leu Cys Ser Met Tyr
                85                  90                  95
Ala Pro Val Cys Thr Val Leu Glu Gln Ala Ile Pro Pro Cys Arg Ser
                100                 105                 110
Ile Cys Glu Arg Ala Arg Gln Gly Cys Glu Ala Leu Met Asn Lys Phe
                115                 120                 125
Gly Phe Gln Trp Pro Glu Arg Leu Arg Cys Glu His Phe Pro Arg His
                130                 135                 140
Gly Ala Glu Gln Ile Cys Val Gly Gln Asn His Ser Glu Asp Gly Ala
145                 150                 155                 160
Pro Ala Leu Leu Thr Thr Ala Pro Pro Gly Leu Gln Pro Gly Ala
                165                 170                 175
Gly Gly Thr Pro Gly Gly Pro Gly Gly Gly Ala Pro Pro Arg Tyr
                180                 185                 190
Ala Thr Leu Glu His Pro Phe His Cys Pro Arg Val Leu Lys Val Pro
                195                 200                 205
Ser Tyr Leu Ser Tyr Lys Phe Leu Gly Glu Arg Asp Cys Ala Ala Pro
                210                 215                 220
Cys Glu Pro Ala Arg Pro Asp Gly Ser Met Phe Phe Ser Gln Glu Glu
225                 230                 235                 240
Thr Arg Phe Ala Arg Leu Trp Ile Leu Thr Trp Ser Val Leu Cys Cys
                245                 250                 255
Ala Ser Thr Phe Phe Thr Val Thr Thr Tyr Leu Val Asp Met Gln Arg
                260                 265                 270
Phe Arg Tyr Pro Glu Arg Pro Ile Ile Phe Leu Ser Gly Cys Tyr Thr
                275                 280                 285
Met Val Ser Val Ala Tyr Ile Ala Gly Phe Val Leu Gln Glu Arg Val
                290                 295                 300
Val Cys Asn Glu Arg Phe Ser Glu Asp Gly Tyr Arg Thr Val Val Gln
```

```
                305                 310                 315                 320

Gly Thr Lys Lys Glu Gly Cys Thr Ile Leu Phe Met Met Leu Tyr Phe
                325                 330                 335

Phe Ser Met Ala Ser Ser Ile Trp Trp Val Ile Leu Ser Leu Thr Trp
                340                 345                 350

Phe Leu Ala Ala Gly Met Lys Trp Gly His Glu Ala Ile Glu Ala Asn
                355                 360                 365

Ser Gln Tyr Phe His Leu Ala Ala Trp Ala Val Pro Ala Val Lys Thr
                370                 375                 380

Ile Thr Ile Leu Ala Met Gly Gln Ile Asp Gly Asp Leu Leu Ser Gly
385                 390                 395                 400

Val Cys Phe Val Gly Leu Asn Ser Leu Asp Pro Leu Arg Gly Phe Val
                405                 410                 415

Leu Ala Pro Leu Phe Val Tyr Leu Phe Ile Gly Thr Ser Phe Leu Leu
                420                 425                 430

Ala Gly Phe Val Ser Leu Phe Arg Ile Arg Thr Ile Met Lys His Asp
                435                 440                 445

Gly Thr Lys Thr Glu Lys Leu Glu Arg Leu Met Val Arg Ile Gly Val
                450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
                485                 490                 495

Gln His Cys Lys Ser Leu Ala Ile Pro Cys Pro Ala His Tyr Thr Pro
                500                 505                 510

Arg Met Ser Pro Asp Phe Thr Val Tyr Met Ile Lys Tyr Leu Met Thr
                515                 520                 525

Leu Ile Val Gly Ile Thr Ser Gly Phe Trp Ile Trp Ser Gly Lys Thr
                530                 535                 540

Leu His Ser Trp Arg Lys Phe Tyr Thr Arg Leu Thr Asn Ser Arg His
545                 550                 555                 560

Gly Glu Thr Thr Val
                565

(2) INFORMATION FOR SEQ ID NO: 9:

(i) SEQUENCE CHARACTERISTICS:
        (A) LENGTH: 585 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Met Ala Arg Pro Asp Pro Ser Ala Pro Pro Ser Leu Leu Leu Leu Leu
1               5                   10                  15

Leu Ala Gln Leu Val Gly Arg Ala Ala Ala Ser Lys Ala Pro Val
                20                  25                  30

Cys Gln Glu Ile Thr Val Pro Met Cys Arg Gly Ile Gly Tyr Asn Leu
                35                  40                  45

Thr His Met Pro Asn Gln Phe Asn His Asp Thr Gln Asp Glu Ala Gly
                50                  55                  60

Leu Glu Val His Gln Phe Trp Pro Leu Val Glu Ile Gln Cys Ser Pro
65                  70                  75                  80

Asp Leu Arg Phe Phe Leu Cys Thr Met Tyr Thr Pro Ile Cys Leu Pro
```

-continued

```
                  85                  90                  95
Asp Tyr His Lys Pro Leu Pro Pro Cys Arg Ser Val Cys Glu Arg Ala
            100                 105                 110
Lys Ala Gly Cys Ser Pro Leu Met Arg Gln Tyr Gly Phe Ala Trp Pro
            115                 120                 125
Glu Arg Met Ser Cys Asp Arg Leu Pro Val Leu Gly Arg Asp Ala Glu
            130                 135             140
Val Leu Cys Met Asp Tyr Asn Arg Ser Glu Ala Thr Thr Ala Pro Pro
145                 150                 155                 160
Arg Pro Phe Pro Ala Lys Pro Thr Leu Pro Gly Pro Pro Gly Ala Pro
                165                 170                 175
Ala Ser Gly Gly Glu Cys Pro Ala Gly Gly Pro Phe Val Cys Lys Cys
                180                 185                 190
Arg Glu Pro Phe Val Pro Ile Leu Lys Glu Ser His Pro Leu Tyr Asn
            195                 200                 205
Lys Val Arg Thr Gly Gln Val Pro Asn Cys Ala Val Pro Cys Tyr Gln
            210                 215                 220
Pro Ser Phe Ser Ala Asp Glu Arg Thr Phe Ala Thr Phe Trp Ile Gly
225                 230                 235                 240
Leu Trp Ser Val Leu Cys Phe Ile Ser Thr Ser Thr Val Ala Thr
                245                 250                 255
Phe Leu Ile Asp Met Asp Thr Phe Arg Tyr Pro Glu Arg Pro Ile Ile
                260                 265                 270
Phe Leu Ser Ala Cys Tyr Leu Cys Val Ser Leu Gly Phe Leu Val Arg
                275                 280                 285
Leu Val Val Gly His Ala Ser Val Ala Cys Ser Arg Glu His Asn His
            290                 295                 300
Ile His Tyr Glu Thr Thr Gly Pro Ala Leu Cys Thr Ile Val Phe Leu
305                 310                 315                 320
Leu Val Tyr Phe Phe Gly Met Ala Ser Ser Ile Trp Trp Val Ile Leu
                325                 330                 335
Ser Leu Thr Trp Phe Leu Ala Ala Ala Met Lys Trp Gly Asn Glu Ala
                340                 345                 350
Ile Ala Gly Tyr Gly Gln Tyr Phe His Leu Ala Ala Trp Leu Ile Pro
                355                 360                 365
Ser Val Lys Ser Ile Thr Ala Leu Ala Leu Ser Ser Val Asp Gly Asp
            370                 375                 380
Pro Val Ala Gly Ile Cys Tyr Val Gly Asn Gln Asn Leu Asn Ser Leu
385                 390                 395                 400
Arg Arg Phe Val Leu Gly Pro Leu Val Leu Tyr Leu Leu Val Gly Thr
                405                 410                 415
Leu Phe Leu Leu Ala Gly Phe Val Ser Leu Phe Arg Ile Arg Ser Val
                420                 425                 430
Ile Lys Gln Gly Gly Thr Lys Thr Asp Lys Leu Glu Lys Leu Met Ile
            435                 440                 445
Arg Ile Gly Ile Phe Thr Leu Leu Tyr Thr Val Pro Ala Ser Ile Val
450                 455                 460
Val Ala Cys Tyr Leu Tyr Glu Gln His Tyr Arg Glu Ser Trp Glu Ala
465                 470                 475                 480
Ala Leu Thr Cys Ala Cys Pro Gly His Asp Thr Gly Gln Pro Arg Ala
                485                 490                 495
Lys Pro Glu Tyr Trp Val Leu Met Leu Lys Tyr Phe Met Cys Leu Val
            500                 505                 510
```

```
Val Gly Ile Thr Ser Gly Val Trp Ile Trp Ser Gly Lys Thr Val Glu
            515                 520                 525

Ser Trp Arg Arg Phe Thr Ser Arg Cys Cys Arg Pro Arg Gly
    530                 535                 540

His Lys Ser Gly Gly Ala Met Ala Ala Gly Asp Tyr Pro Glu Ala Ser
545                 550                 555                 560

Ala Ala Leu Thr Gly Arg Thr Gly Pro Pro Gly Pro Ala Ala Thr Tyr
                565                 570                 575

His Lys Gln Val Ser Leu Ser His Val
                580                 585

(2) INFORMATION FOR SEQ ID NO: 10:

(i) SEQUENCE CHARACTERISTICS:
        (A) LENGTH: 666 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Met Ala Val Ser Trp Ile Val Phe Asp Leu Trp Leu Leu Thr Val Phe
1               5                   10                  15

Leu Gly Gln Ile Gly Gly His Ser Leu Phe Ser Cys Glu Pro Ile Thr
                20                  25                  30

Leu Arg Met Cys Gln Asp Leu Pro Tyr Asn Thr Thr Phe Met Pro Asn
            35                  40                  45

Leu Leu Asn His Tyr Asp Gln Gln Thr Ala Ala Leu Ala Met Glu Pro
50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95

Leu Pro Cys Arg Arg Leu Cys Gln Arg Ala Tyr Ser Glu Cys Ser Lys
            100                 105                 110

Leu Met Glu Met Phe Gly Val Pro Trp Pro Glu Asp Met Glu Cys Ser
            115                 120                 125

Arg Phe Pro Asp Cys Asp Glu Pro Tyr Pro Arg Leu Val Asp Leu Asn
130                 135                 140

Leu Val Gly Asp Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
                165                 170                 175

Tyr Ser Phe Leu His Val Arg Asp Cys Ser Pro Pro Cys Pro Asn Met
                180                 185                 190

Tyr Phe Arg Arg Glu Glu Leu Ser Phe Ala Arg Tyr Phe Ile Gly Leu
            195                 200                 205

Ile Ser Ile Ile Cys Leu Ser Ala Thr Leu Phe Thr Phe Leu Thr Phe
            210                 215                 220

Leu Ile Asp Val Thr Arg Phe Arg Tyr Pro Glu Arg Pro Ile Ile Phe
225                 230                 235                 240

Tyr Ala Val Cys Tyr Met Met Val Ser Leu Ile Phe Phe Ile Gly Phe
                245                 250                 255

Leu Leu Glu Asp Arg Val Ala Cys Asn Ala Ser Ser Pro Ala Gln Tyr
            260                 265                 270
```

-continued

```
Lys Ala Ser Thr Val Thr Gln Gly Ser His Asn Lys Ala Cys Thr Met
            275                 280                 285

Leu Phe Met Val Leu Tyr Phe Phe Thr Met Ala Gly Ser Val Trp Trp
        290                 295                 300

Val Ile Leu Thr Ile Thr Trp Phe Leu Ala Ala Val Pro Lys Trp Gly
305                 310                 315                 320

Ser Glu Ala Ile Glu Lys Lys Ala Leu Leu Phe His Ala Ser Ala Trp
                325                 330                 335

Gly Ile Pro Gly Thr Leu Thr Ile Ile Leu Leu Ala Met Asn Lys Ile
            340                 345                 350

Glu Gly Asp Asn Ile Ser Gly Val Cys Phe Val Gly Leu Tyr Asp Val
        355                 360                 365

Asp Ala Leu Arg Tyr Phe Val Leu Ala Pro Leu Cys Leu Tyr Val Val
    370                 375                 380

Val Gly Val Ser Leu Leu Leu Ala Gly Ile Ile Ser Leu Asn Arg Val
385                 390                 395                 400

Arg Ile Glu Ile Pro Leu Glu Lys Glu Asn Gln Asp Lys Leu Val Lys
                405                 410                 415

Phe Met Ile Arg Ile Gly Val Phe Ser Ile Leu Tyr Leu Val Pro Leu
            420                 425                 430

Leu Val Val Ile Gly Cys Tyr Phe Tyr Glu Gln Ala Tyr Arg Gly Ile
        435                 440                 445

Trp Glu Thr Thr Trp Ile Gln Glu Arg Cys Arg Glu Tyr His Ile Pro
    450                 455                 460

Cys Pro Tyr Gln Val Thr Gln Met Ser Arg Pro Asp Leu Ile Leu Phe
465                 470                 475                 480

Leu Met Lys Tyr Leu Met Ala Leu Ile Val Gly Ile Pro Ser Ile Phe
                485                 490                 495

Trp Val Gly Ser Lys Lys Thr Cys Phe Glu Trp Ala Ser Phe Phe His
            500                 505                 510

Gly Arg Arg Lys Lys Glu Ile Val Asn Glu Ser Arg Gln Val Leu Gln
        515                 520                 525

Glu Pro Asp Phe Ala Gln Ser Leu Leu Arg Asp Pro Asn Thr Pro Ile
    530                 535                 540

Ile Arg Lys Ser Arg Gly Thr Ser Thr Gln Gly Thr Ser Thr His Ala
545                 550                 555                 560

Ser Ser Thr Gln Leu Ala Met Val Asp Asp Gln Arg Ser Lys Ala Gly
                565                 570                 575

Ser Val His Ser Lys Val Ser Ser Tyr His Gly Ser Leu His Arg Ser
            580                 585                 590

Arg Asp Gly Arg Tyr Thr Pro Cys Ser Tyr Arg Gly Met Glu Glu Arg
        595                 600                 605

Leu Pro His Gly Ser Met Ser Arg Leu Thr Asp His Ser Arg His Ser
    610                 615                 620

Ser Ser His Arg Leu Asn Glu Gln Ser Arg His Ser Ser Ile Arg Asp
625                 630                 635                 640

Leu Ser Asn Asn Pro Met Thr His Ile Thr His Gly Thr Ser Met Asn
                645                 650                 655

Arg Val Ile Glu Glu Asp Gly Thr Ser Ala
            660                 665
```

(2) INFORMATION FOR SEQ ID NO: 11:

(i) SEQUENCE CHARACTERISTICS:
    (A) LENGTH: 537 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 11:

```
Met Ala Trp Pro Gly Thr Gly Pro Ser Ser Arg Gly Ala Pro Gly Gly
1               5                   10                  15

Val Gly Leu Arg Leu Gly Leu Leu Gln Phe Leu Leu Leu Leu Leu Arg
            20                  25                  30

Pro Thr Leu Gly Phe Gly Asp Glu Glu Arg Arg Cys Asp Pro Ile
        35                  40                  45

Arg Ile Ala Met Cys Gln Asn Leu Gly Tyr Asn Val Thr Lys Met Pro
    50                  55                  60

Asn Leu Val Gly His Glu Leu Gln Thr Asp Ala Glu Leu Gln Leu Thr
65                  70                  75                  80

Thr Phe Thr Pro Leu Ile Gln Tyr Gly Cys Ser Ser Gln Leu Gln Phe
                85                  90                  95

Phe Leu Cys Ser Val Tyr Val Pro Met Cys Thr Glu Lys Ile Asn Ile
            100                 105                 110

Pro Ile Gly Pro Cys Gly Gly Met Cys Leu Ser Val Lys Arg Arg Cys
            115                 120                 125

Glu Pro Val Leu Arg Glu Phe Gly Phe Ala Trp Pro Asp Thr Leu Asn
130                 135                 140

Cys Ser Lys Phe Pro Pro Gln Asn Asp His Asn His Met Cys Met Glu
145                 150                 155                 160

Gly Pro Gly Asp Glu Glu Val Pro Leu Pro His Lys Thr Pro Ile Gln
                165                 170                 175

Pro Gly Glu Glu Cys His Ser Val Gly Ser Asn Ser Asp Gln Tyr Ile
            180                 185                 190

Trp Val Lys Arg Ser Leu Asn Cys Val Leu Lys Cys Gly Tyr Asp Ala
            195                 200                 205

Gly Leu Tyr Ser Arg Ser Ala Lys Glu Phe Thr Asp Ile Trp Met Ala
        210                 215                 220

Val Trp Ala Ser Leu Cys Phe Ile Ser Thr Thr Phe Thr Val Leu Thr
225                 230                 235                 240

Phe Leu Ile Asp Ser Ser Arg Phe Ser Tyr Pro Glu Arg Pro Ile Ile
                245                 250                 255

Phe Leu Ser Met Cys Tyr Asn Ile Tyr Ser Ile Ala Tyr Ile Val Arg
            260                 265                 270

Leu Thr Val Gly Arg Glu Arg Ile Ser Cys Asp Phe Glu Glu Ala Ala
        275                 280                 285

Glu Pro Val Leu Ile Gln Glu Gly Leu Lys Asn Thr Gly Cys Ala Ile
        290                 295                 300

Ile Phe Leu Leu Met Tyr Phe Phe Gly Met Ala Ser Ser Ile Trp Trp
305                 310                 315                 320

Val Ile Leu Thr Leu Thr Trp Phe Leu Ala Ala Gly Leu Lys Trp Gly
                325                 330                 335

His Glu Ala Ile Glu Met His Ser Ser Tyr Phe His Ile Ala Ala Trp
            340                 345                 350

Ala Ile Pro Ala Val Lys Thr Ile Val Ile Leu Ile Met Arg Leu Val
        355                 360                 365
```

-continued

```
Asp Ala Asp Glu Leu Thr Gly Leu Cys Tyr Val Gly Asn Gln Asn Leu
        370                 375                 380

Asp Ala Leu Thr Gly Phe Val Val Ala Pro Leu Phe Thr Tyr Leu Val
385                 390                 395                 400

Ile Gly Thr Leu Phe Ile Ala Ala Gly Leu Val Ala Leu Phe Lys Ile
                    405                 410                 415

Arg Ser Asn Leu Gln Lys Asp Gly Thr Lys Thr Asp Lys Leu Glu Arg
                420                 425                 430

Leu Met Val Lys Ile Gly Val Phe Ser Val Leu Tyr Thr Val Pro Ala
                435                 440                 445

Thr Cys Val Ile Ala Cys Tyr Phe Tyr Glu Ile Ser Asn Trp Ala Leu
            450                 455                 460

Phe Arg Tyr Ser Ala Asp Asp Ser Asn Met Ala Val Glu Met Leu Lys
465                 470                 475                 480

Ile Phe Met Ser Leu Leu Val Gly Ile Thr Ser Gly Met Trp Ile Trp
                485                 490                 495

Ser Ala Lys Thr Leu His Thr Trp Gln Lys Cys Ser Asn Arg Leu Val
                500                 505                 510

Asn Ser Gly Lys Val Lys Arg Glu Lys Arg Gly Asn Gly Trp Val Lys
                515                 520                 525

Pro Gly Lys Gly Asn Glu Thr Val Val
530                 535
```

(2) INFORMATION FOR SEQ ID NO: 12:

(i) SEQUENCE CHARACTERISTICS:
        (A) LENGTH: 709 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Met Glu Arg Ser Pro Phe Leu Leu Ala Cys Ile Leu Pro Leu Val
1               5                   10                  15

Arg Gly His Ser Leu Phe Thr Cys Glu Pro Ile Thr Val Pro Arg Cys
                20                  25                  30

Met Lys Met Thr Tyr Asn Met Thr Phe Phe Pro Asn Leu Met Gly His
                35                  40                  45

Tyr Asp Gln Gly Ile Ala Ala Val Glu Met Gly His Phe Leu His Leu
50                  55                  60

Ala Asn Leu Glu Cys Ser Pro Asn Ile Glu Met Phe Leu Cys Gln Ala
65                  70                  75                  80

Phe Ile Pro Thr Cys Thr Glu Gln Ile His Val Val Leu Pro Cys Arg
                    85                  90                  95

Lys Leu Cys Glu Lys Ile Val Ser Asp Cys Lys Lys Leu Met Asp Thr
                    100                 105                 110

Phe Gly Ile Arg Trp Pro Glu Glu Leu Glu Cys Asn Arg Leu Pro His
                115                 120                 125

Cys Asp Asp Thr Val Pro Val Thr Ser His Pro His Thr Glu Leu Ser
            130                 135                 140

Gly Pro Gln Lys Lys Ser Asp Gln Val Pro Arg Asp Ile Gly Phe Trp
145                 150                 155                 160

Cys Pro Lys His Leu Arg Thr Ser Gly Asp Gln Gly Tyr Arg Phe Leu
                    165                 170                 175
```

```
Gly Ile Glu Gln Cys Ala Pro Pro Cys Pro Asn Met Tyr Phe Lys Ser
                180                 185                 190

Asp Glu Leu Asp Phe Ala Lys Ser Phe Ile Gly Ile Val Ser Ile Phe
            195                 200                 205

Cys Leu Cys Ala Thr Leu Phe Thr Phe Leu Thr Phe Leu Ile Asp Val
        210                 215                 220

Arg Arg Phe Arg Tyr Pro Glu Arg Pro Ile Ile Tyr Tyr Ser Val Cys
225                 230                 235                 240

Tyr Ser Ile Val Ser Leu Met Tyr Phe Val Gly Phe Leu Leu Gly Asn
                245                 250                 255

Ser Thr Ala Cys Asn Lys Ala Asp Glu Lys Leu Glu Leu Gly Asp Thr
            260                 265                 270

Val Val Leu Gly Ser Lys Asn Lys Ala Cys Ser Val Val Phe Met Phe
        275                 280                 285

Leu Tyr Phe Phe Thr Met Ala Gly Thr Val Trp Trp Val Ile Leu Thr
        290                 295                 300

Ile Thr Trp Phe Leu Ala Ala Gly Arg Lys Trp Ser Cys Glu Ala Ile
305                 310                 315                 320

Glu Gln Lys Ala Val Trp Phe His Ala Val Ala Trp Gly Ala Pro Gly
                325                 330                 335

Phe Leu Thr Val Met Leu Leu Ala Met Asn Lys Val Glu Gly Asp Asn
            340                 345                 350

Ile Ser Gly Val Cys Phe Val Gly Leu Tyr Asp Leu Asp Ala Ser Arg
        355                 360                 365

Tyr Phe Val Leu Leu Pro Leu Cys Leu Cys Val Phe Val Gly Leu Ser
        370                 375                 380

Leu Leu Leu Ala Gly Ile Ile Ser Leu Asn His Val Arg Gln Val Ile
385                 390                 395                 400

Gln His Asp Gly Arg Asn Gln Glu Lys Leu Lys Lys Phe Met Ile Arg
                405                 410                 415

Ile Gly Val Phe Ser Gly Leu Tyr Leu Val Pro Leu Val Thr Leu Leu
            420                 425                 430

Gly Cys Tyr Val Tyr Glu Leu Val Asn Arg Ile Thr Trp Glu Met Thr
        435                 440                 445

Trp Phe Ser Asp His Cys His Gln Tyr Arg Ile Pro Cys Pro Tyr Gln
        450                 455                 460

Ala Asn Pro Lys Ala Arg Pro Glu Leu Ala Leu Phe Met Ile Lys Tyr
465                 470                 475                 480

Leu Met Thr Leu Ile Val Gly Ile Ser Ala Val Phe Trp Val Gly Ser
                485                 490                 495

Lys Lys Thr Cys Thr Glu Trp Ala Gly Phe Phe Lys Arg Asn Arg Lys
            500                 505                 510

Arg Asp Pro Ile Ser Glu Ser Arg Arg Val Leu Gln Glu Ser Cys Glu
        515                 520                 525

Phe Phe Leu Lys His Asn Ser Lys Val Lys His Lys Lys His Gly
        530                 535                 540

Ala Pro Gly Pro His Arg Leu Lys Val Ile Ser Lys Ser Met Gly Thr
545                 550                 555                 560

Ser Thr Gly Ala Thr Thr Asn His Gly Thr Ser Ala Met Ala Ile Ala
                565                 570                 575

Asp His Asp Tyr Leu Gly Gln Glu Thr Ser Thr Glu Val His Thr Ser
            580                 585                 590

Pro Glu Ala Ser Val Lys Glu Gly Arg Ala Asp Arg Ala Asn Thr Pro
```

-continued

```
                 595                 600                 605
Ser Ala Lys Asp Arg Asp Cys Gly Glu Ser Ala Gly Pro Ser Ser Lys
    610                 615                 620

Leu Ser Gly Asn Arg Asn Gly Arg Glu Ser Arg Ala Gly Gly Leu Lys
625                 630                 635                 640

Glu Arg Ser Asn Gly Ser Glu Gly Ala Pro Ser Glu Gly Arg Val Ser
                645                 650                 655

Pro Lys Ser Ser Val Pro Glu Thr Gly Leu Ile Asp Cys Ser Thr Ser
            660                 665                 670

Gln Ala Ala Ser Ser Pro Glu Pro Thr Ser Leu Lys Gly Ser Thr Ser
        675                 680                 685

Leu Pro Val His Ser Ala Ser Arg Ala Arg Lys Glu Gln Gly Ala Gly
    690                 695                 700

Ser His Ser Asp Ala
705
```

(2) INFORMATION FOR SEQ ID NO: 13:

(i) SEQUENCE CHARACTERISTICS:
      (A) LENGTH: 572 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 13:

```
Met Arg Gly Pro Gly Thr Ala Ala Ser His Ser Pro Leu Gly Leu Cys
1               5                   10                  15

Ala Leu Val Leu Ala Leu Leu Gly Ala Leu Pro Thr Asp Thr Arg Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
    50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Ala Gly Gly Ser Pro
                165                 170                 175

Thr Ala Tyr Pro Thr Ala Pro Tyr Leu Pro Asp Pro Pro Phe Thr Ala
            180                 185                 190

Met Ser Pro Ser Asp Gly Arg Gly Arg Leu Ser Phe Pro Phe Ser Cys
        195                 200                 205

Pro Arg Gln Leu Lys Val Pro Pro Tyr Leu Gly Tyr Arg Phe Leu Gly
    210                 215                 220

Glu Arg Asp Cys Gly Ala Pro Cys Glu Pro Gly Arg Ala Asn Gly Leu
```

```
                225                 230                 235                 240
Met Tyr Phe Lys Glu Glu Arg Arg Phe Ala Arg Leu Trp Val Gly
                245                 250                 255
Val Trp Ser Val Leu Ser Cys Ala Ser Thr Leu Phe Thr Val Leu Thr
                260                 265                 270
Tyr Leu Val Asp Met Arg Arg Phe Ser Tyr Pro Glu Arg Pro Ile Ile
                275                 280                 285
Phe Leu Ser Gly Cys Tyr Phe Met Val Ala Val His Val Ala Gly
    290                 295                 300
Phe Leu Leu Glu Asp Arg Ala Val Cys Val Glu Arg Phe Ser Asp Asp
305                 310                 315                 320
Gly Tyr Arg Thr Val Ala Gln Gly Thr Lys Lys Glu Gly Cys Thr Ile
                325                 330                 335
Leu Phe Met Val Leu Tyr Phe Gly Met Ala Ser Ser Ile Trp Trp
                340                 345                 350
Val Ile Leu Ser Leu Thr Trp Phe Leu Ala Ala Gly Met Lys Trp Gly
                355                 360                 365
His Glu Ala Ile Glu Ala Asn Ser Gln Tyr Phe His Leu Ala Ala Trp
    370                 375                 380
Ala Val Pro Ala Val Lys Thr Ile Thr Ile Leu Ala Met Gly Gln Val
385                 390                 395                 400
Asp Gly Asp Leu Leu Ser Gly Val Cys Tyr Val Gly Leu Ser Ser Val
                405                 410                 415
Asp Ala Leu Arg Gly Phe Val Leu Ala Pro Leu Phe Val Tyr Leu Phe
                420                 425                 430
Ile Gly Thr Ser Phe Leu Leu Ala Gly Phe Val Ser Leu Phe Arg Ile
                435                 440                 445
Arg Thr Ile Met Lys His Asp Gly Thr Lys Thr Glu Lys Leu Glu Lys
    450                 455                 460
Leu Met Val Arg Ile Gly Val Phe Ser Val Leu Tyr Thr Val Pro Ala
465                 470                 475                 480
Thr Ile Val Leu Ala Cys Tyr Phe Tyr Glu Gln Ala Phe Arg Glu His
                485                 490                 495
Trp Glu Arg Thr Trp Leu Leu Gln Thr Cys Lys Ser Tyr Ala Val Pro
                500                 505                 510
Cys Pro Pro Arg His Phe Ser Pro Met Ser Pro Asp Phe Thr Val Phe
                515                 520                 525
Met Ile Lys Tyr Leu Met Thr Met Ile Val Gly Ile Thr Thr Gly Phe
                530                 535                 540
Trp Ile Trp Ser Gly Lys Thr Leu Gln Ser Trp Arg Arg Phe Tyr His
545                 550                 555                 560
Arg Leu Ser His Ser Ser Lys Gly Glu Thr Ala Val
                565                 570

(2) INFORMATION FOR SEQ ID NO: 14:

(i) SEQUENCE CHARACTERISTICS:
        (A) LENGTH: 685 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Met Glu Trp Gly Tyr Leu Leu Glu Val Thr Ser Leu Leu Ala Ala Leu
```

-continued

```
1               5               10              15
Ala Val Leu Gln Arg Ser Ser Gly Ala Ala Ala Ser Ala Lys Glu
            20              25              30
Leu Ala Cys Gln Glu Ile Thr Val Pro Leu Cys Lys Gly Ile Gly Tyr
            35              40              45
Asn Tyr Thr Tyr Met Pro Asn Gln Phe Asn His Asp Thr Gln Asp Glu
            50              55              60
Ala Gly Leu Glu Val His Gln Phe Trp Pro Leu Val Glu Ile Gln Cys
65              70              75              80
Ser Pro Asp Leu Lys Phe Phe Leu Cys Ser Met Tyr Thr Pro Ile Cys
            85              90              95
Leu Glu Asp Tyr Lys Lys Pro Leu Pro Pro Cys Arg Ser Val Cys Glu
            100             105             110
Arg Ala Lys Ala Gly Cys Ala Pro Leu Met Arg Gln Tyr Gly Phe Ala
            115             120             125
Trp Pro Asp Arg Met Arg Cys Asp Arg Leu Pro Glu Gln Gly Asn Pro
            130             135             140
Asp Thr Leu Cys Met Asp Tyr Asn Arg Thr Asp Leu Thr Thr Ala Ala
145             150             155             160
Pro Ser Pro Pro Arg Arg Leu Pro Pro Pro Pro Gly Glu Gln
            165             170             175
Pro Pro Ser Gly Ser Gly His Ser Arg Pro Pro Gly Ala Arg Pro Pro
            180             185             190
His Arg Gly Gly Ser Ser Arg Gly Ser Gly Asp Ala Ala Ala Pro
            195             200             205
Pro Ser Arg Gly Gly Lys Ala Arg Pro Pro Gly Gly Ala Ala Pro
            210             215             220
Cys Glu Pro Gly Cys Gln Cys Arg Ala Pro Met Val Ser Val Ser Ser
225             230             235             240
Glu Arg His Pro Leu Tyr Asn Arg Val Lys Thr Gly Gln Ile Ala Asn
            245             250             255
Cys Ala Leu Pro Cys His Asn Pro Phe Phe Ser Gln Asp Glu Arg Ala
            260             265             270
Phe Thr Val Phe Trp Ile Gly Leu Trp Ser Val Leu Cys Phe Val Ser
            275             280             285
Thr Phe Ala Thr Val Ser Thr Phe Leu Ile Asp Met Glu Arg Phe Lys
            290             295             300
Tyr Pro Glu Arg Pro Ile Ile Phe Leu Ser Ala Cys Tyr Leu Phe Val
305             310             315             320
Ser Val Gly Tyr Leu Val Arg Leu Val Ala Gly His Glu Lys Val Ala
            325             330             335
Cys Ser Gly Gly Ala Pro Gly Ala Gly Gly Arg Gly Gly Ala Gly Gly
            340             345             350
Ala Ala Ala Ala Gly Ala Gly Ala Gly Arg Gly Ala Ser Ser Pro
            355             360             365
Gly Ala Arg Gly Glu Tyr Glu Glu Leu Gly Ala Val Glu Gln His Val
            370             375             380
Arg Tyr Glu Thr Thr Gly Pro Ala Leu Cys Thr Val Val Phe Leu Leu
385             390             395             400
Val Tyr Phe Phe Gly Met Ala Ser Ser Ile Trp Trp Val Ile Leu Ser
            405             410             415
Leu Thr Trp Phe Leu Ala Ala Gly Met Lys Trp Gly Asn Glu Ala Ile
            420             425             430
```

```
Ala Gly Tyr Ser Gln Tyr Phe His Leu Ala Ala Trp Leu Val Pro Ser
        435                 440                 445

Val Lys Ser Ile Ala Val Leu Ala Leu Ser Ser Val Asp Gly Asp Pro
    450                 455                 460

Val Ala Gly Ile Cys Tyr Val Gly Asn Gln Ser Leu Asp Asn Leu Arg
465                 470                 475                 480

Gly Phe Val Leu Ala Pro Leu Val Ile Tyr Leu Phe Ile Gly Thr Met
                485                 490                 495

Phe Leu Leu Ala Gly Phe Val Ser Leu Phe Arg Ile Arg Ser Val Ile
            500                 505                 510

Lys Gln Gln Gly Gly Pro Thr Lys Thr His Lys Leu Glu Lys Leu Met
        515                 520                 525

Ile Arg Leu Gly Leu Phe Thr Val Leu Tyr Thr Val Pro Ala Ala Val
        530                 535                 540

Val Val Ala Cys Leu Phe Tyr Glu Gln His Asn Arg Pro Arg Trp Glu
545                 550                 555                 560

Ala Thr His Asn Cys Pro Cys Leu Arg Asp Leu Gln Pro Asp Gln Ala
                565                 570                 575

Arg Arg Pro Asp Tyr Ala Val Phe Met Leu Lys Tyr Phe Met Cys Leu
            580                 585                 590

Val Val Gly Ile Thr Ser Gly Val Trp Val Trp Ser Gly Lys Thr Leu
        595                 600                 605

Glu Ser Trp Arg Ala Leu Cys Thr Arg Cys Cys Trp Ala Ser Lys Gly
        610                 615                 620

Ala Ala Val Gly Ala Gly Ala Gly Ser Gly Pro Gly Gly Ser Gly
625                 630                 635                 640

Pro Gly Pro Gly Gly Gly Gly His Gly Gly Gly Gly Ser Leu
                645                 650                 655

Tyr Ser Asp Val Ser Thr Gly Leu Thr Trp Arg Ser Gly Thr Ala Ser
                660                 665                 670

Ser Val Ser Tyr Pro Lys Gln Met Pro Leu Ser Gln Val
        675                 680                 685

(2) INFORMATION FOR SEQ ID NO: 15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 15:

CCTGTAGATC TCCC                                                   14

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 16:

ATTTCGGAGA TCTACAGG                                               18

(2) INFORMATION FOR SEQ ID NO: 17:

(i) SEQUENCE CHARACTERISTICS:
```

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 17:

TTTTTTTTTT TTTTTNS                                              17

(2) INFORMATION FOR SEQ ID NO: 18:

(i) SEQUENCE CHARACTERISTICS:
        (A) LENGTH: 1308 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GAATTCCGGT CCGGAGTCAG TGCCGCGCGC CCGCCGCCCC GCGCCTTCCT GCTCGCCGCA        60

CCTCCGGGAG CCGGGGCGCA CCCAGCCCGC AGCGCCGCCT CCCCGCCCGC GCCGCCTCCG       120

ACCGCAGGCC GAGGGCCGCC ACTGGCCGGG GGGACCGGGC AGCAGCTTGC GGCCGCGGAG       180

CGGGCAACGC TGGGGACTGC GCCTTTTGTC CCCGGAGGTC CCTGGAAGTT TGCGGCAGGA       240

CGCGCGCGGG GAGGCGGCGG AGGCAGCCCC GACGTCGCGG AGAACAGGGC GCAGAGCCGG       300

CATGGGCATC GGGCGCAGCG AGGGGGGCCG CCGCGGGGCA GCCCTGGGCG TGCTGCTGGC       360

GCTGGGCGCG GCGCTTCTGG CCGTGGGCTC GGCCAGCGAG TACGACTACG TGAGCTTCCA       420

GTCGGACATC GGCCCGTACC AGAGCGGGCG CTTCTACACC AAGCCACCTC AGTGCGTGGA       480

CATCCCCGCG GACCTGCGGC TGTGCCACAA CGTGGGCTAC AAGAAGATGG TGCTGCCCAA       540

CCTGCTGGAG CACGAGACCA TGGCGGAGGT GAAGCAGCAG GCCAGCAGCT GGGTGCCCCT       600

GCTCAACAAG AACTGCCACG CCGGCACCCA GGTCTTCCTC TGCTCGCTCT TCGCCCCCGT       660

CTGCCTGGAC CGGCCCATCT ACCCGTGTCG CTGGCTCTGC GAGGCCGTGC GCGACTCGTG       720

CGAGCCGGTC ATGCAGTTCT TCGGCTTCTA CTGGCCCGAG ATGCTTAAGT GTGACAAGTT       780

CCCCGAGGGG GACGTCTGCA TCGCCATGAC GCCGCCCAAT CCCACCGAAG CCTCCAAGCC       840

CCAAGGCACA ACGGTGTGTC CTCCCTGTGA CAACGAGTTG AAATCTGAGG CCATCATTGA       900

ACATCTCTGT GCCAGCGAGT TTGCACTGAG GATGAAAATA AAGAAGTGA AAAAGAAAA       960

TGGCGACAAG AAGATTGTCC CCAAGAAGAA GAAGCCCCTG AAGTTGGGGC CCATCAAGAA      1020

GAAGGACCTG AAGAAGCTTG TGCTGTACCT GAAGAATGGG GCTGACTGTC CCTGCCACCA      1080

GCTGGACAAC CTCAGCCACC ACTTCCTCAT CATGGGCCGC AAGGTGAAGA GCCAGTACTT      1140

GCTGACGGCC ATCCACAAGT GGGACAAGAA AAACAAGGAG TTCAAAAACT TCATGAAGAA      1200

AATGAAAAAC CATGAGTGCC CCACCTTTCA GTCCGTGTTT AAGTGATTCT CCCGGGGGCA      1260

GGGTGGGGAG GGAGCCTCGG GTGGGGTGGG AGCGGGGGGC CGGAATTC                1308

(2) INFORMATION FOR SEQ ID NO: 19:

(i) SEQUENCE CHARACTERISTICS:
        (A) LENGTH: 19 amino acids
        (B) TYPE: amino acid
        (C) STRANDEDNESS: single
        (D) TOPOLOGY: linear -continued (xi) SEQUENCE DESCRIPTION: SEQ ID NO: 19:

```
Ile Ala Met Thr Pro Pro Asn Pro Thr Glu Ala Ser Lys Pro Gln Gly
1               5                   10                  15
Thr Thr Val
```

FAMILY OF GENES ENCODING APOPTOSIS-RELATED PEPTIDES, PEPTIDES ENCODED THEREBY AND METHODS OF USE THEREOF

The present application is a continuation of U.S. patent application Ser. No. 08/937,067, filed Sep. 24, 1997, now U.S. Pat. No. 6,433,155, which claims priority under 35 U.S.C. 119(e) to U.S. Provisional Application Ser. No. 60/026,603, filed Sep. 24, 1996, now abandoned, and U.S. Provisional Application Ser. No. 60/028,363, filed Oct. 11, 1996, now abandoned. U.S. patent application Ser. No. 08/937,067, U.S. Provisional Application Ser. No. 60/026,603 and U.S. Provisional Application Ser. No. 60/028,363 are incorporated herein by this reference in their entirety.

TECHNICAL FIELD

The present invention relates to the field of diagnosing and treating conditions related to apoptosis, or programmed cell death. More specifically, it relates to the identification and characterization of a novel gene family, the expression of which is associated with apoptosis.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death can be initiated by a wide variety of signals, including hormones, serum growth factor deprivation, chemotherapeutic agents, ionizing radiation and infection by human immunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; Kruman et al. (1991) *J. Cell. Physiol.* 148:267–273; Ameisen and Capron (1991) *Immunology Today* 12:102; and Sheppard and Ascher (1992) *J. AIDS* 5:143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) *FASEB J.* 6:2450; and Cohen and Duke (1992) *Ann. Rev. Immunol.* 10:267. The blebs, small, membrane-encapsulated spheres that pinch off of the surface of apoptotic cells, may continue to produce superoxide radicals which damage surrounding cell tissue and may be involved in inflammatory processes.

While apoptosis is a normal cellular event, it can also be induced by pathological conditions and a variety of injuries. Apoptosis is involved in a wide variety of conditions including, but not limited to, cardiovascular disease; cancer regression; immunoregulation; viral diseases; anemia; neurological disorders; gastrointestinal disorders, including but not limited to, diarrhea and dysentery; diabetes; hair loss; rejection of organ transplants; prostate hypertrophy; obesity; ocular disorders; stress; and aging.

Genes which have been shown to activate the apoptosis pathway in tumor cells include the FAS antigen, TNFα and TNFβ. See, e.g. Tomei and Cope et al. in Apoptosis II: The Molecular Basis of Apoptosis in Disease (1994) Cold Spring Harbor Laboratory Press. In the nematode *C. elegans,* mutations in the genes ced-3 and ced-4 prevent autonomous cell death during development. Yuan and Horvitz (1990) *Dev. Biol.* 138:33. A mutation which activates the nematode gene ced-9 prevents cell death during development, whereas mutations that inactive this gene promote programmed cell death. In mammalian cells, the p-53 gene has been shown to induce apoptosis in some cells, but not others.

Apoptosis-inhibiting genes under investigation include bcl-2 which was isolated from B-cell lymphomas and blocks apoptosis without affecting cell proliferation. See, e.g., Tsujimoto et al. *Science* 226:1087; Hockenberry et al. (1990) *Nature* 348:334. The mechanism by which bcl-2 inhibits apoptosis is not known. Mcl-1, expressed in myeloid cells, exhibits sequence similarity to bcl-2 and is believed to be involved in regulating apoptosis. Kozopas et al. (1993) *Proc. Natl. Acad. Sci. USA* 90:3516.

Members of a large family of putative transmembrane receptors related to the *Drosophila melanogaster* tissue polarity gene frizzled have been cloned recently. See, Wang et al. (1995) *J. Biol. Chem.* 271:4468. Frizzled family members are found in organisms as diverse as nematodes and humans and are expressed in a variety of tissues and during embryonic development. In *Drosophila, frizzled* mutations affect the polarity of structures, such as sensory bristles, on the body surface. The precise functions and clinical significance of the frizzled family in other species remains largely unknown.

All references cited herein, both supra and infra, are hereby incorporated by reference herein.

SUMMARY OF THE INVENTION

The present invention encompasses isolated polynucleotides, polypeptides and antibodies derived from or reactive with the products of the novel apoptosis-related genes. The invention also encompasses uses of these compositions.

Accordingly, one aspect of the invention is polynucleotides encoding polypeptides of the SARP family. Representative polypeptides are those having the amino acid sequence of SEQ. ID. NO: 2, 4, 6 or 7. The invention likewise encompasses polynucleotides encoding peptides having substantial homology to the amino acid sequence of SEQ. ID. NO: 2, 4, 6 or 7.

In another aspect, the invention provides isolated polynucleotides that are comprised of a region of at least 15 contiguous nucleotides, where these nucleotides are capable of forming a stable duplex with a polynucleotide encoding sequence of SEQ. ID. NO: 1, 3, 5 or 18.

Another aspect of the invention is cloning and expression vectors comprising the polynucleotides of the invention. Also included are host cells comprising the polynucleotides of the invention.

In another aspect, the invention comprises polypeptides of at least 11 amino acid residues of SEQ. ID. NO: 2, 4, 6 or 7 and further comprises polypeptides substantially homologous to 11 amino acid residues of SEQ. ID. NO: 2, 4, 6 or 7. The invention also provides fusion polypeptides comprising a polypeptide of the present invention.

The invention also provides for polyclonal or monoclonal antibodies which specifically bind to the polypeptides of the invention. There are termed αSARP antibodies.

In another aspect, methods of detecting the polynucleotides of the invention are provided. These methods comprise contacting a biological sample under conditions that permit the formation of a stable complex, and detecting any stable complexes formed.

Another aspect of the invention is methods of detecting the SARP family of proteins. These methods entail the steps of contacting a biological sample obtained from an individual with an αSARP antibody of the invention under conditions that permit the stable antigen-antibody complex and detecting stable complex formed, if any.

Also provided are methods for treatment of apoptosis by administration of a therapeutically effective amount of the polynucleotides and/or polypeptides of the invention to a patient in need of such treatment. The methods include making a composition for treatment of conditions related to apoptosis. Other methods using these compositions include preventing apoptosis in cultured cells, methods of increasing organ preservation for subsequent organ transplantation and in situ preservation for bypass operations, e.g., heart, liver, lungs, brain, etc., and methods of treating dermatological conditions in which apoptosis is implicated.

Also provided are methods for the detection of disease by providing a test sample of bodily fluid; assaying the test sample for the presence of a gene product of an hsarp gene; and comparing the amount of gene product detected in the test sample to the amount of gene product detected in a non-diseased sample of the same tissue type as the test sample. Assaying encompasses, but is not limited to, nucleic acid hybridization and antibody-antigen interactions.

In an additional embodiment of the present invention, a method of treatment of a patient is provided, comprising administering to the patient a therapeutically effective amount of a pharmaceutically acceptable composition comprising a component selected from the group comprising a sarp or antisense-hsarp polynucleotide or a SARP polypeptide or SARP antibody. The method can be a method of treating apoptosis related conditions. In a specific embodiment, the patient is suffering from a condition related to cancer, including, but not limited to, cancer of the mammary tissue, the prostate or the prostate epithelial tissue. In an additional embodiment, the composition contains a sarp polynucleotide or the gene product of that polynucleotide, a SARP polypeptide.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

BRIEF DESCRIPTION OF THE DRAWINGS

FIG. 1A shows alignment of hSARP2 predicted amino acid sequence to frizzled proteins. [SEQ. ID. NOS: 7–9].

FIG. 1B shows a comparison of the amino acid sequence of mSARP1 (SEQ. ID. NO: 2) to various frizzled proteins (SEQ. ID. NOS: 10–14).

MODE(S) FOR CARRYING OUT THE INVENTION

Figure 1A:
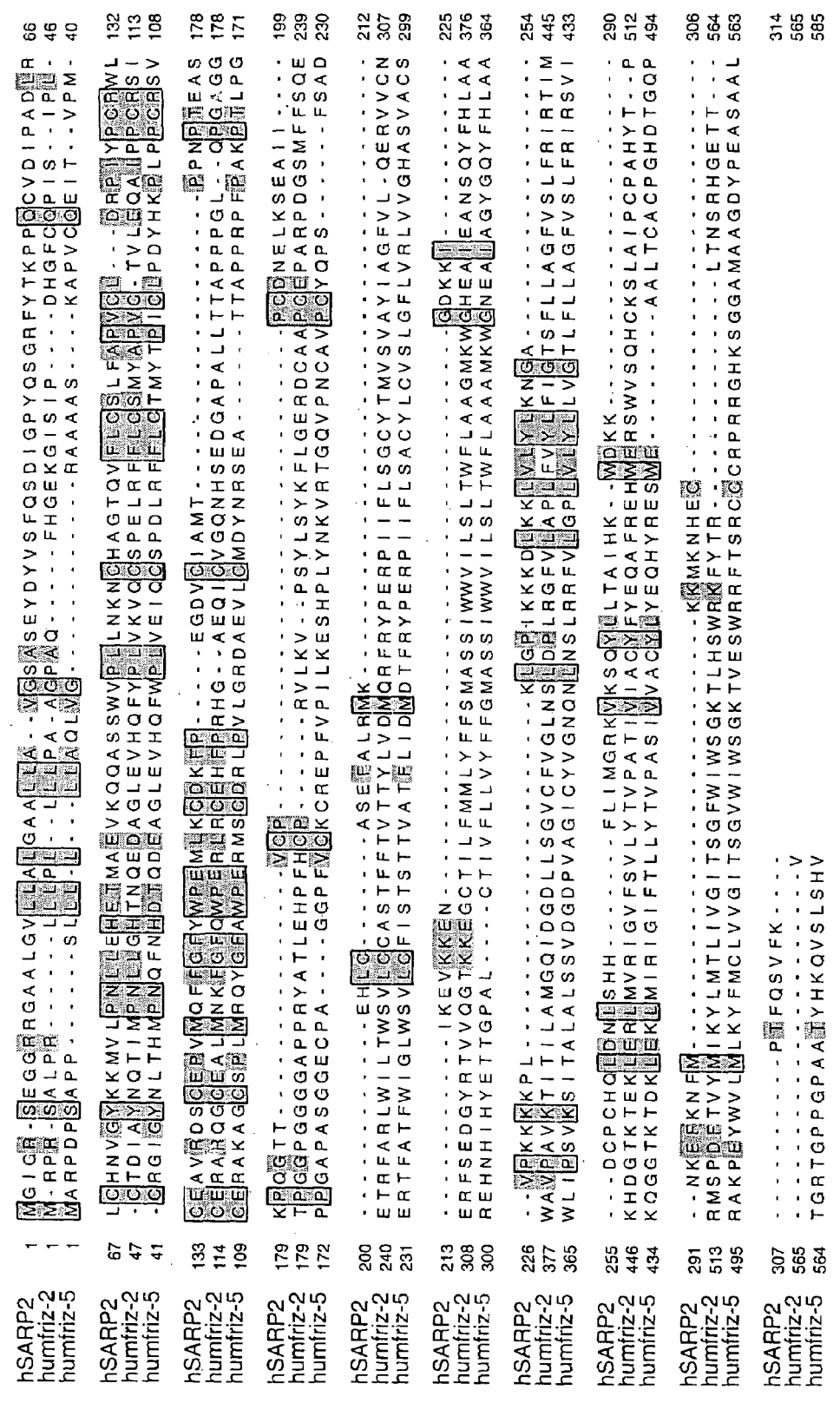
Figure 1B:
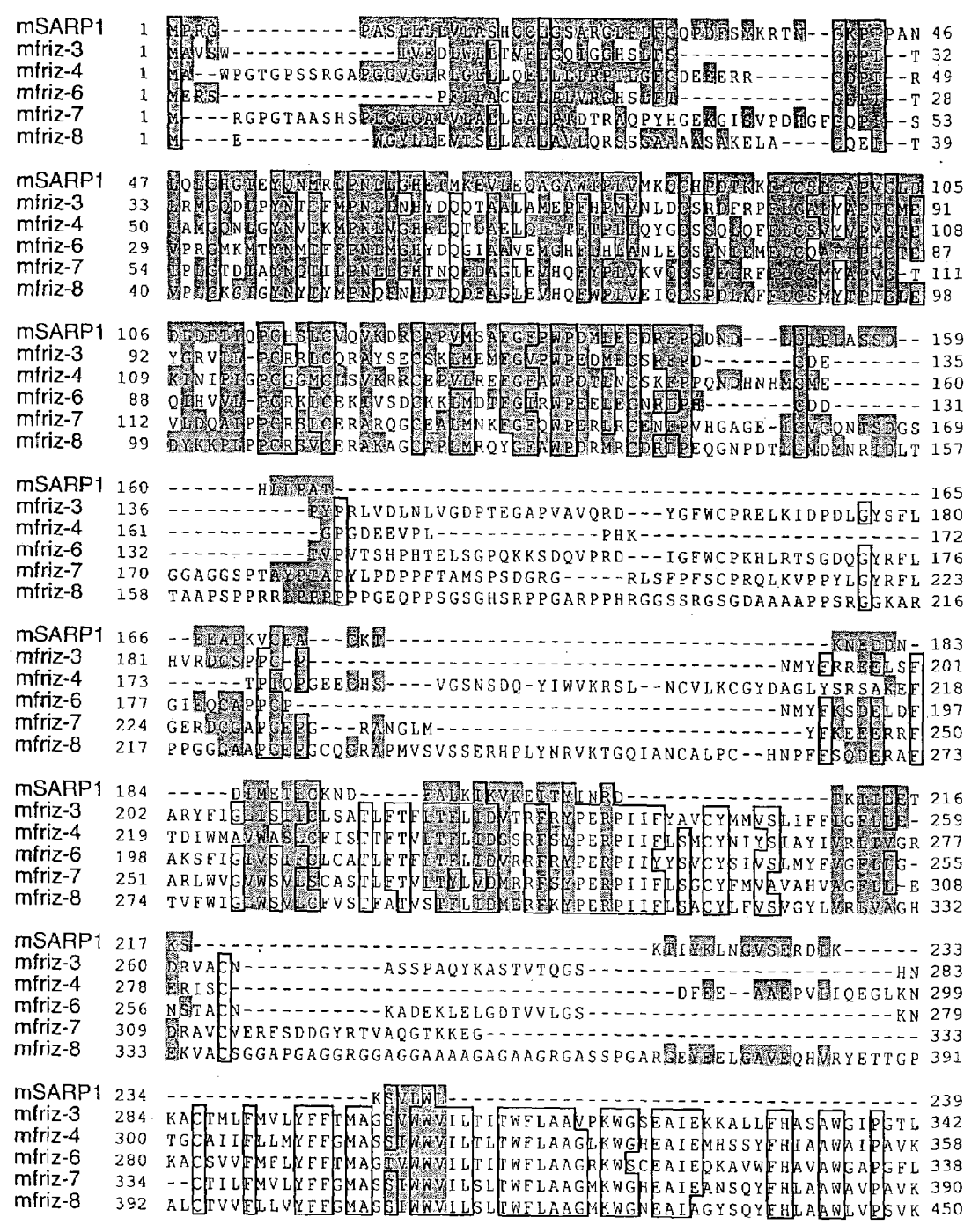
Figure 2:
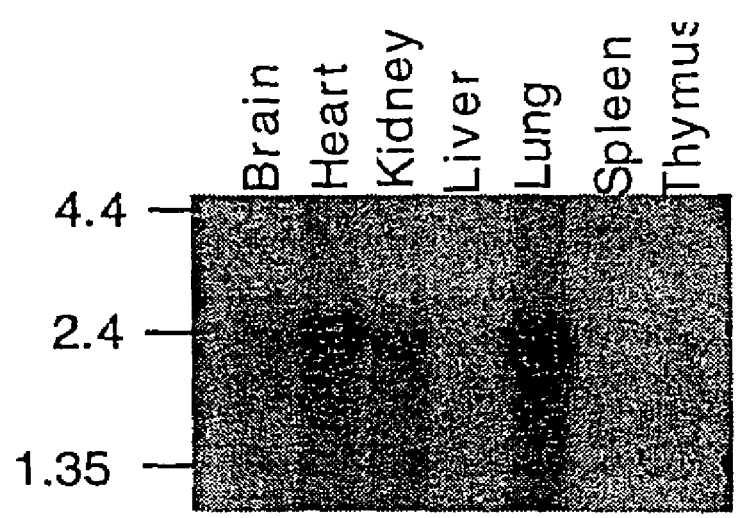
FIG. 2 is a Northern blot depicting tissue specific expression of msarp1 in various mouse tissues. RNAs were isolated from different tissues resolved on 1.2% formaldehyde-agarose gel, transferred to nylon membrane and probed by msarp1 at high stringency.

Disclosed herein is a new gene family, the expression of which is associated with apoptosis. The genes are termed "sarp" (secreted apoptosis related protein). msarp genes are derived from murine sources whereas hsarp genes are derived from human sources. These genes, including msarp1, hsarp2, hsarp1 and hsarp3, encode novel proteins which belong to the family of proteins termed "SARP". The hsarp2 gene is expressed in a variety of tissues. When hsarp2 was inserted into an expression vector and transfected into human cell lines, it increased the percentage of cells undergoing apoptosis in culture. The hsarp2 gene is expressed in exponentially growing non-transformed cell lines, and repressed in quiescent ones. Increased expression of hsarp2 has been shown to increase programmed cell death in a breast carcinoma cell line in a dose dependent manner. A BLAST search of Gene Bank revealed significant homology between the novel gene family and members of the "Frizzled Like" gene family (see FIG. 1B, SEQ. ID. NOS: 10–14). The frizzled-like gene family encodes cell membrane proteins having seven transmembrane domains with unknown functions. It was previously shown that Wnt and frizzled proteins interact. Bhanot et al. (1996) Nature 382:225–230. Multiple sequence alignment to human frizzled-like proteins showed that the novel family is most homologous in the extracellular N-terminal domains of frizzled-like proteins, with little homology in the transmembrane region. SARPs have now been shown to interfere with the Wnt-frizzled protein interaction and modify apoptosis by effecting cell-cell and cell-extracellular matrix signaling.

We have cloned a family of novel genes from mouse cells and from human heart and pancreas cDNA libraries. The expression of these genes is associated with the early stages of apoptosis. The mouse gene, termed msarp1, contains a single open reading frame which encodes a predicted protein product of 295 amino acids which is secreted. msarp1 is expressed at high levels in heart, lung and is upregulated in cardiomyocytes subjected to injuries which trigger apoptosis. Transcription of msarp1 is also significantly induced in 10T1/2 cells which reached quiescence, a state of arrested cell growth which is characterized by increased resistance to apoptotic stimuli.

The novel gene family also includes three human genes, termed hsarp2, hsarp1 and hsarp3. hsarp1 is closely homologous to msarp1 and has one open reading frame (ORF) which encodes a 212 amino acid polypeptide, termed hSARP1. hsarp3 encodes a protein of 316 amino acids, termed hSARP3, which is homologous to hSARP2 and mSARP1. hSARP1 is expressed at highest levels in colon, small intestine, pancreas and prostate. hSARP3 is expressed predominately in pancreas.

The hsarp2 cDNA sequence contains 1302 nucleotides and encodes a polypeptide of 314 amino acids having an N-terminal methionine and C-terminal lysine amino acid residues. The full length cDNA sequence includes 301 nucleotides of the 5' untranslated region and 62 nucleotides of 3' untranslated region. The hsarp2 cDNA contains one major open reading frame (ORF) (hSARP2). The ATG start site is found at position 303, and the termination site is at position 1248. When hsarp2 is inserted into an expression vector and transfected into human cell lines, it increases the percentage of cells that undergo apoptosis in culture.

As used herein, "sarp" including msarp1 hsarp1, hsarp2 and hsarp3, refer to the nucleic acid molecules encoding the SARPs, and derivatives and complementary nucleotides thereof. "SARP" including mSARP, hSARP1, hSARP2 and hSARP3 refer to the proteins encoded thereby. Other members of the family can be obtained by the methods described in the Examples presented herein.

The present invention encompasses nucleotide sequences of the new gene family. The nucleotides include, but are not limited to, the cDNA, genome-derived DNA and synthetic or semi-synthetic DNA or RNA. The nucleotide sequence of msarp1 is contained in SEQ. ID. NO: 1; the nucleotide sequence of hsarp1 is contained in SEQ. ID. NO: 3, the sequence of hsarp3 is contained in SEQ. ID. NO: 5, and the nucleotide sequence of hsarp2 is contained in SEQ. ID. NO: 18. As described in the examples herein, the mRNA of this gene family has been detected in a variety of human organs and tissues by Northern blot analysis. Expression of hsarp2 mRNA, for example, was detected in most human tissues probed; in exponentially growing human mammary non-transformed cells and in exponentially growing human normal diploid fibroblast cells.

The term "polynucleotide" is used to mean a polymeric form of nucleotides of any length, which contain deoxyribonucleotides, ribonucleotides, and/or their analogs. The terms "polynucleotide" and "nucleotide" as used herein are used interchangeably. Polynucleotides can have any three-dimensional structure, and can perform any function, known or unknown. The term "polynucleotide" includes double-stranded, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide can be comprised of modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentynyluracil and 2,6-diaminopurine. The use of uracil as a substitute for thymine in a deoxyribonucleic acid is also considered an analogous form of pyrimidine.

If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars can be replaced by phosphonate groups, phosphate groups, protected by standard protecting groups, or activated to prepare additional linkages to additional nucleotides, or can be conjugated to solid supports. The 5' and 3' terminal hydroxy groups can be phosphorylated or substituted with amines or organic capping group moieties of from 1 to 20 carbon atoms. Other hydroxyls can also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

As noted above, one or more phosphodiester linkages can be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1–20 C) optionally containing and ether (—O—) linkage, aryl, alkenyl, cycloalky, cycloalkenyl or araldyl. Not all linkages in a polynucleotide need be identical.

Although conventional sugars and bases will be used in applying the method of the invention, substitution of analogous forms of sugars, purines and pyrimidines can be advantageous in designing a final product, as can alternative backbone structures like a polyamide backbone.

An "antisense" polynucleotide is a sequence complementary to all or part of a functional RNA or DNA. For example, antisense RNA is complementary to sequences of the mRNA copied from the gene.

A "fragment" (also called a "region") of a polynucleotide (i.e., a polynucleotide encoding a sarp) is a polynucleotide comprised of at least 9 contiguous nucleotides of the novel genes. Preferred fragments are comprised of a region encoding at least 5 contiguous amino acid residues, more preferably, at least 10 contiguous amino acid residues, and even more preferably at least 15 contiguous amino acid residues.

The term "recombinant" polynucleotide as used herein intends a polynucleotide of genomic, cDNA, semisynthetic, or synthetic in origin which, by virtue of its origin or manipulation: is not associated with all or a portion of a polynucleotide with which it is associated in nature; is linked to a polynucleotide other than that to which it is linked in nature; or does not occur in nature.

The terms "polypeptide", "oligopeptide", "peptide" and "protein" are used interchangeably herein to refer to polymers of amino acid residues. The polymer can be linear or branched, it can comprise modified amino acid residues, and it can be interrupted by non-amino acid residues. The terms also encompass an amino acid polymer that has been modified naturally or by intervention; for example, by disulfide bond formation, glycosylation, lipidation, acetylation, phosphorylation, or any other manipulation or modification, such as conjugation with a labeling component. Also included within the definition are, for example, polypeptides containing one or more analogs of an amino acid residue (including, for example, unnatural amino acid residues, etc.), as well as other modifications known in the art.

A polypeptide "fragment" (also called a "region") of a SARP is a polypeptide comprising an amino acid sequence of a SARP that has at least 5 contiguous amino acid residues of a sequence of a SARP, more preferably at least 8 contiguous amino acid residues, and even more preferably at least about 10 contiguous amino acid residues. For purposes of this invention, a fragment of a SARP can be identified and characterized by any of the following functions: (a) homology to a SARP; (b) ability to change a percentage of cells undergoing apoptosis; or (c) effect cell death. A SARP fragment can have any, more than one, or all of the above identified functions. Methods for determining these functions (a) through (c) will be described below.

A "fusion polypeptide" is a polypeptide comprising regions in a different position in the sequence than occurs in nature. The regions can normally exist in separate proteins and are brought together in the fusion polypeptide; or they can normally exist in the same protein but are placed in a new arrangement in the fusion polypeptide.

A "functionally equivalent fragment" of a SARP polypeptide or sarp polynucleotide preserves at least one property and/or function of the SARP polypeptides or sarp polynucleotides. For example, the sequences can be varied by adding additional nucleotides or peptides as known in the art, such that the functionality of the sequence is not altered. Other examples are deletion and/or substitution of sequences. Alternatively, the sequences can be varied by substituting nucleotides or amino acid residue, or a combination of addition, deletion, or substitution. As is evident to one of skill in the art, functionality of a polypeptide sequence includes characteristics and/or activities of the sequence, such as antigenicity and effect on the apoptotic pathway. It is also clear that functionality of a polynucleotide sequence depends in part upon its intended use, and any functionality that is preserved in a fragment of a polynucleotide satisfies this definition.

For instance, a "functionally equivalent fragment" of a sarp polynucleotide can be one in which an ability to hybridize is preserved, as the desired polynucleotide can be used as a probe. Alternatively, a "functionally equivalent fragment" of a sarp polynucleotide can mean that the polynucleotide encodes a fragment of a SARP that has a function associated with an intact SARP, and preferably a function associated with apoptosis modulation. A functionally equivalent fragment of the novel polypeptides or polynucleotide can have the same, enhanced, or decreased function when compared to the SARP polypeptides or polynucleotides. Other functions of SARP have been listed above. A functionally equivalent fragment has at least 9 nucleotides or at least 5 amino acids, preferably has at least 15 nucleotides or at least 10 amino acids, even more preferably has at least 25 nucleotides or at least 20 amino acids.

"Stringent conditions" for hybridization of both DNA/DNA and DNA/RNA are as described in Sambrook et al. (1989) MOLECULAR CLONING, A LABORATORY MANUAL, 2nd. Ed., Cold Spring Harbor Laboratory Press. Examples of relevant conditions include (in order of increasing stringency): incubation temperatures of 25° C., 37° C., 50° C., and 68° C.; buffer concentrations of 10×SSC, 6×SSC, 1×SSC (where SSC is 0.15M NaCl and 15 mM citrate buffer) and their equivalent using other buffer systems; formamide concentrations of 0%, 25%, 50% and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

A "stable duplex" of polynucleotides, or a "stable complex" formed between any two or more components in a biochemical reaction, refers to a duplex or complex that is sufficiently long-lasting to persist between formation of the duplex or complex and subsequent detection, including any optional washing steps or other manipulation that can take place in the interim.

The term "antibody" refers to an immunoglobulin protein or antigen binding fragment that recognizes a particular antigen. Preferably, the antibodies of the present invention (termed αSARP) are not specific to members of the Frizzled family of proteins. Antibodies can be monoclonal or polyclonal. The generation and characterization of antibodies is within the skill of an ordinary artisan. The term "antibody" further encompasses proteins which have been coupled to another compound by chemical conjugation, or by mixing with an excipient or an adjuvant. The term antigen binding fragment includes any peptide that binds to the SARP in a specific manner. Typically, these derivatives include such immunoglobulin fragments as Fab, F(ab')2, Fab', scfv (both monomeric and polymeric forms) and isolated H and L chains. The term αSARP encompasses antigen binding fragments. An antigen binding fragment retains the specificity of the intact immunoglobulin, although avidity and/or affinty can be altered.

The antigen binding fragments (also termed "derivatives" herein) are typically generated by genetic engineering, although they can alternatively be obtained by other methods and combinations of methods. This classification includes, but is not limited to, engineered peptide fragments and fusion peptides. Preferred compounds include polypeptide fragments of the CRDs, antibody fusion proteins comprising cytokine effector components, antibody fusion proteins comprising adjuvants or drugs, and single-chain V region proteins. Additionally, the antigen binding fragments of this invention can be used as diagnostic and imaging reagents.

Scfv can be produced either recombinantly or synthetically. For synthetic production of scfv, an automated synthesizer can be used. For recombinant production of scfv, a suitable plasmid containing polynucleotide that encodes the scfv can be introduced into a suitable host cell, either eukaryotic, such as yeast, plant, insect or mammalian cells, or prokaryotic, such as *Escherichia coli,* and the expressed protein can be isolated using standard protein purification techniques.

A particularly useful system for the production of scfvs is plasmid pET-22b(+) (Novagen, Madison, Wis.) in *E. coli.* pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

Conditions of expression should ensure that the scfv assumes optimal tertiary structure. Depending on the plasmid used (especially the activity of the promoter) and the host cell, it may be necessary to modulate the rate of production. For instance, use of a weaker promoter, or expression at lower temperatures, may be necessary to optimize production of properly folded scfv in prokaryotic systems; or, it may be preferably to express scfv in eukaryotic cells.

The invention also encompasses antibodies conjugated to a chemically functional moiety. Typically, the moiety is a label capable of producing a detectable signal. These conjugated antibodies are useful, for example, in detection and imaging systems. Such labels are known in the art and include, but are not limited to, radioisotopes, enzymes, fluorescent compounds, chemiluminescent compounds, bioluminescent compounds substrate cofactors and inhibitors. See, for examples of patents teaching the use of such labels, U.S. Pat. Nos. 3,817,837; 3,850,752; 3,939,350; 3,996,345; 4,277,437; 4,275,149; and 4,366,241. The moieties can be covalently linked to the antibodies, recombinantly linked, or conjugated to the antibodies through a secondary reagent, such as a second antibody, protein A, or a biotin-avidin complex.

Methods of antibody production and isolation are well known in the art. See, for example, Harlow and Lane (1988) *Antibodies: A Laboratory Manual,* Cold Spring Harbor Laboratory, New York. Purification methods include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. The antibodies can also be purified on affinity columns comprising a SARP protein; for example, in the form of a purified Ab1 or Ab3. Preferably, the antibodies can be purified using Protein-A-CL-Sepharose™ 4B chromatography followed by chromatography on a DEAE-Sepharose™ 4B ion exchange column.

A "cell line" or "cell culture" denotes higher eukaryotic cells grown or maintained in vitro. It is understood that the descendants of a cell may not be completely identical (either morphologically, genotypically, or phenotypically) to the parent cell.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. Suitable cloning vectors are known in the art e.g., those for use in bacterial, mammalian, yeast and insect expression systems. Specific vectors and suitable host cells are discussed for instance in Galesa and Ramji Vectors, John Wiley & Sons (1994). Examples of prokaryotic host cells appropriate for use in this invention include, but are not limited to, *E. coli* and *Bacillus subtilis.* Examples of eukaryotic host cells include, but are not limited to, avian, insect, plant and animal cells such as C057, HeLa and CHO cells.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "signal sequence" is a short amino acid sequence that directs newly synthesized secretory or membrane proteins to and through cellular membranes such as the endoplasmic reticulim. Signal sequences are typically in the N-terminal portion of a polypeptide and are cleaved after the polypeptide has crossed the membrane.

A "gene product" encompasses any product or products of transcription or translation of a gene, including without limitation mRNAs, tRNAs and proteins.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide. A promoter which is linked to a coding sequence with which it is not naturally linked is a heterologous promoter.

The heterologous polynucleotide can comprise a sequence of interest for purposes of therapy, and can optionally be in the form of an expression cassette. As used herein, a vector need not be capable of replication in the ultimate target cell or subject. The term includes cloning vectors for the replication of a polynucleotide, and expression vectors for translation of a polynucleotide encoding sequence. Also included are viral vectors, which comprise a polynucleotide encapsidated or enveloped in a viral particle.

Suitable cloning vectors can be constructed according to standard techniques, or can be selected from a large number of cloning vectors available in the art. While the cloning vector selected can vary according to the host cell intended to be used, useful cloning vectors will generally have the ability to self-replicate, can possess a single target for a particular restriction endonuclease, or can carry genes for a marker that can be used in selecting clones containing the vector. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide encoding a polypeptide of interest. The polynucleotide encoding the polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) can be derived from the sarp genes, or they can be heterologous (i.e., derived from other genes or other organisms). A polynucleotide sequence encoding a signal peptide can also be included to allow a polypeptide to cross or lodge in cell membranes or be secreted from the cell.

A number of expression vectors suitable for expression in eukaryotic cells including yeast, avian, and mammalian cells are known in the art. One example of an expression vector is pcDNA3 (Invitrogen, San Diego, Calif., in which transcription is driven by the cytomegalovirus (CMV) early promoter/enhancer. This vector also contains recognition sites for multiple restriction enzymes for insertion of the polynucleotide of interest. Another example of an expression vector (system) is the baculovirus/insect system.

A vector of this invention can contain one or more polynucleotides encoding a polypeptide. It can also contain polynucleotide sequences encoding other polypeptides that enhance, facilitate, or modulate the desired result, such as lymphokines, including, but not limited to, IL-2, IL-4 and GM-CSF. A preferred lymphokine is GM-CSF. Preferred GM-CSF constructs are those which have been deleted for the AU-rich elements from the 3' untranslated regions and sequences in the 5' untranslated region that are capable of forming a hairpin loop.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus, which is discussed below). The choice of means of introducing vectors or polynucleotides will often depend features of the on the host cell. Once introduced into a suitable host cell, expression of a polypeptide can be determined using any assay known in the art. For example, presence of polypeptide can be detected by RIA or ELISA of the culture supernatant (if the polypeptide is secreted) or cell lysates.

An "isolated" or "purified" polynucleotide, polypeptide or antibody is one that is substantially free of the materials with which it is associated in nature. By substantially free is meant at least 50%, preferably at least 70%, more preferably at least 80%, and even more preferably at least 90% free of the materials with which it is associated in nature.

A biological "sample" encompasses a variety of sample types obtained from an individual and is typically used in a diagnostic procedure or assay. The definition encompasses blood and other liquid samples of biological origin, solid tissue samples such as a biopsy specimens or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term encompasses various kinds of clinical samples obtained from any species, and also includes, but is not limited to, cells in culture, cell supernatants, cell lysates, serum, plasma, biological fluid, and tissue samples.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival in the absence of treatment.

"Apoptosis-associated" refers to any condition in which the apoptosis pathway leading to cell death is involved. These conditions can be normal or pathogenic biological events and can be initiated by a wide variety of signals, including, but not limited to, hormones, serum growth factor deprivation, chemotherapeutic agents, ionizing radiation and human immunodeficiency virus (HIV) infection.

Infarctions are caused by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs to tissues surrounding the infarct upon reperfusion of blood to the area; thus, modulation by a biological modifier-induced change in endogenous production or by in vivo transfection, could be effective at reducing the severity of damage caused by heart attacks and stroke.

Chemotherapeutic agents, ionizing radiation, and infection by HIV also initiate the apoptosis pathway. Currently, a variety of food supplements have been used in an attempt to ameliorate the gastrointestinal disorders that accompany chemotherapy, radiation and AIDS. These supplements generally contain carbohydrates, fats and plant protein hydrolysates. See, e.g., Tomei and Cope et al. in Apoptosis: The Molecular Basis of Cell Death (1991) Cold Spring Harbor Laboratory Press. PCT Publication No. WO 95/15173 describes plant-derived delipidated extracts capable of producing anti-apoptotic effect. Thus, affecting the molecular basis of apoptosis-associated conditions has therapeutic utility in numerous clinical situations.

"Antisense therapy" is a method of attenuating gene expression using a therapeutic polynucleotide. The therapeutic polynucleotide comprises a sequence or complementary sequence that is capable of forming a stable hybrid with either the target gene itself, or more typically the heteronuclear or messenger RNA transcribed therefrom. Typically, the therapeutic polynucleotide is operatively linked to a suitable promoter. The antisense polynucleotide need not be the exact complement of the target polynucleotide to be effective, so long as stable hybrids form under physiological conditions. A moderate number of mutations, insertions or deletions can be present, depending on the length of the antisense polynucleotide. The antisense polynucleotide need not hybridize with the entire target gene-coding sequence, although longer hybridizing regions are preferred over shorter ones.

An "effective amount" is an amount sufficient to effect beneficial or desired clinical results. An effective amount can be administered in one or more doses. In terms of treatment, an "effective amount" of polynucleotide, and/or polypeptide is an amount sufficient to palliate, ameliorate, stabilize, reverse, slow or delay the progression of apoptosis-associated disease states or otherwise reduce the pathological consequences of the disease. Detection and measurement of these indicators of efficacy are discussed below. The effective amount is generally determined by the physician on a case-by-case basis and is within the skill of one in the art. Several factors are typically taken into account when determining an appropriate dosage. These factors include age, sex and weight of the patient, the condition being treated, the severity of the condition and the form of the antibody being administered. For instance, the concentration of scfv need not be as high as that of native antibodies in order to be therapeutically effective.

An "individual" is a vertebrate, preferably a mammal, more preferably a human. Mammals include farm and sport animals, and pets.

The invention thus includes isolated nucleotide encoding (or complementary thereto) polypeptides substantially identical to (i.e. having at least 90% sequence identity to) SARPs as exemplified by SEQ ID NOS: 2, 4, 6 and 7, with any amino acid substitutions preferably being conservative, or an allelic variant thereof, or to a homologue of SARP from a species other than man. The invention therefore includes, for example, either or both strands of a cDNA encoding a SARP or an allelic variant thereof; a recombinant DNA which is incorporated into a vector, into an autonomously replicating plasmid or virus, or into the genomic DNA of a prokaryotic or eukaryotic cell; or genomic DNA fragments (e.g. produced by PCR or restriction endonuclease treatment of human or other genomic DNA). It also includes a recombinant DNA which is part of a hybrid gene encoding additional polypeptide.

The isolated DNA can be incorporated into a vector (e.g., a virus, phage or plasmid) which can be introduced by transfection or infection into a cell. Suitable vectors include any known in the art, including, but not limited to, those for use in bacterial, mammalian, yeast and insect expression systems. Specific vectors are known in the art and need not be described in detail herein. The vector can include one or more expression control sequences, in which case the cell transfected with the vector is capable of expressing the polypeptide. The vectors can also provide inducible promoters for expression of sarps. Inducible promoters are those which do not allow constitutive expression of the gene but rather, permit expression only under certain circumstances. Such promoters can be induced by a variety of stimuli including, but not limited to, exposure of a cell containing the vector to a ligand, metal ion, other chemical or change in temperature.

These promoters can also be cell-specific, that is, inducible only in a particular cell type and often only during a specific period of time. The promoter can further be cell cycle specific, that is, induced or inducible only during a particular stage in the cell cycle. The promoter can be both cell type specific area cell cycle specific. Any inducible promoter known in the art is suitable for use in the present invention.

Polynucleotides comprising a desired sequence can be inserted into a suitable vector, and the vector in turn can be introduced into a suitable host cell for replication and amplification. Polynucleotides can be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, it can be obtained by using an DNA-dependent RNA polymerase.

The invention includes modifications to sarp DNA sequences such as deletions, substitutions and additions particularly in the non-coding regions of genomic DNA. Such changes are useful to facilitate cloning and modify gene expression. Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses functionally equivalent variants and derivatives of sarps which can enhance, decrease or not significantly affect the properties of SARPs. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of SARPs is encompassed by the present invention.

Techniques for nucleic acid manipulation useful for the practice of the present invention are described in a variety of references, including but not limited to, *Molecular Cloning: A Laboratory Manual,* 2nd ed., Vol. 1-3, eds. Sambrook et al. Cold Spring Harbor Laboratory Press (1989); and *Current Protocols in Molecular Biology,* eds. Ausubel et al., Greene Publishing and Wiley-Interscience: New York (1987) and periodic updates.

Also within the invention is an isolated polynucleotide of at least 15 nucleotides in length, preferably at least 30, more preferably at least 100, and most preferably at least 500, including (a) DNA encoding a SARP, (b) the complement thereof; or a double stranded DNA including both (a) and (b). Multiple copies of this isolated DNA (useful, for example, as a hybridization probe or PCR primer) can be produced synthetically or by recombinant means, by transfecting a cell with a vector containing this DNA.

The invention also includes a purified preparations of SARP peptides, or fragments of these peptides that comprise an antigenic polypeptide containing at least 10 amino acid residues of the peptide (preferably at least 11, more preferably at least 14, and most preferably at least 18), which polypeptide fragment contains an epitope of the peptide such that an antibody raised against the fragment (or against a conjugate of the polypeptide and, if necessary, a carrier molecule) forms an immune complex with the peptide itself. Purification or isolation of SARPs expressed either by the recombinant DNA or from biological sources can be accomplished by any method known in the art. Generally, substantially purified proteins are those which are free of other, contaminating cellular substances, particularly proteins. Preferably, the purified peptides are more than eighty percent pure and most preferably more than ninety-five percent pure.

Suitable methods of protein purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

The invention further comprises suitable antibodies are generated by using a SARP as an antigen or, preferably, peptides encompassing regions of SARPs that lack substantial homology to the other gene products such as the Frizzled proteins. Such an antibody can either be polyclonal or monoclonal, and is generated by standard methods including the step of immunizing an animal with an antigen containing an antigenic portion of at least one SARP.

Also encompassed within the invention are hybrid polypeptides containing: (1) SARP or an antigenic fragment thereof, covalently attached to (2) a second polypeptide. Such hybrid polypeptides can be made by a number of standard techniques well known to those of ordinary skill, including recombinant methods, in which case the covalent attachment is a peptide bond, or chemical conjugation in which case the covalent attachment is another type of bond, such as a disulfide bond. Linking a SARP or an antigenic fragment thereof to a second polypeptide provides a means for readily isolating the hybrid from a mixture of proteins, by the use of an affinity column to which the second polypeptide (e.g. glutathione transferase) binds directly. Such hybrid polypeptides can also have the advantage of increased immunogenicity relative to SARP or a fragment thereof, so that antibodies are more readily obtained.

Both the isolated nucleotides of the invention and the antibodies of the invention are useful in detecting SARP expression. Any method for detecting specific mRNA species is suitable for use in this method. This is easily accomplished using PCR. Preferably, the primers chosen for PCR correspond to the regions of the sarp genes that lack substantial homology to other genes. Alternatively, Northern blots can be utilized to detect sarp mRNA by using probes specific to these genes. Methods of utilizing PCR and Northern blots are known in the art and are not described in detail herein.

Transgenic animals containing the sarp nucleotides are also encompassed by the invention. Methods of making transgenic animals are known in the art and need not be described in detail herein. For a review of methods used to make transgenic animals, see, e.g. PCT publication no. WO 93/04169. Preferably, such animals express recombinant sarps under control of a cell-specific and, even more preferably, a cell cycle specific promoter.

In another embodiment, diagnostic methods are provided to detect the expression of the novel gene family either at the protein level or the mRNA level. Abnormal levels of SARPs are likely to be found in the tissues of patients with diseases associated with inappropriate apoptosis; diagnostic methods are therefore useful for detecting and monitoring biological conditions associated with such apoptosis defects.

Detection methods are also useful for monitoring the success of SARP-related therapies. Both the isolated sarp nucleotides and the antibodies of the invention are useful in diagnostic methods. One such diagnostic method includes the steps of providing a test cell (e.g. in the form of a tissue section or a cell preparation) from a given type of tissue; contacting the mRNA of the test cell with a nucleic acid probe containing a sequence antisense (i.e. complementary to the sense strand of) a segment of a sarp gene. The segment is at least 15 nucleotides in length, preferably at least 20, more preferably at least 30, even more preferably at least 40 and most preferably at least 100 nucleotides in length. The amount of hybridization of the probe to the mRNA of the test cell is compared to the amount of hybridization of the probe to the mRNA of a normal control (i.e. non-apoptotic) cell from the same type of tissue. An increased amount of hybridization in the test cell is an indication that the test cell will have an increased incidence of apoptosis. The assay can be conveniently carried out using standard techniques of in situ hybridization or Northern analysis.

The antibody-based assays of the invention are comparable to the above. The proteins of the test cell, or from a fluid bathing the test cell, are contacted with an antibody (polyclonal or monoclonal) specific for a SARP, and the amount of immunocomplex formed with such proteins is compared with the amount formed by the same antibody with the proteins of a normal control cell (or fluid bathing a normal control cell) from the same type of tissue as the test cell.

In another embodiment, treatment of apoptosis-associated conditions are provided. The invention thus encompasses ex vivo transfection with the sarp gene family, in which cells removed from animals including man are transfected with vectors encoding SARPs or antisense sarps and reintroduced into animals. Suitable transfected cells include individual cells or cells contained within whole tissues. In addition, ex vivo transfection can include the transfection of cells derived from an animal other than the animal or human subject into which the cells are ultimately introduced. Such grafts include, but are not limited to, allografts, xenografts, and fetal tissue transplantation.

The present invention also encompasses antisense therapy to attenuate levels of SARP. Antisense polynucleotides need not be the exact complement of the target polynucleotide to be effective, so long as stable hybrids form under physiological conditions. A moderate number of mutations, insertions or deletions can be present, depending on the length of the antisense polynucleotide. Preferably, the complementary sequence of the antisense polynucleotide is 50% identical to that of the target, including base differences, insertions, and deletions. More preferably, the sequences are about 75% identical; even more preferably they are about 85% identical; still more preferably they are about 95% identical; and most preferably, they are completely identical. The antisense polynucleotide need not hybridize with the entire SARP encoding sequence, although longer hybridizing regions are preferred over shorter ones. Preferably, the hybridizing region is at least about 30 bases in length; more preferably it is at least about 60 bases; even more preferably it is at least about 100 bases; more preferably it is at least about 200 bases or more.

Essentially any cell or tissue type can be treated in this manner. Suitable cells include, but are not limited to, cardiomyocytes and lymphocytes. As an example, in treatment of HIV-infected patients by the above-described method, the white blood cells are removed from the patient and sorted to yield the CD4+ cells. The CD4+ cells are then transfected with a vector encoding either SARP or antisense to sarp and reintroduced into the patient. Alternatively, the unsorted lymphocytes can be transfected with a recombinant vector having at least one sarp-modulator under the control of a cell-specific promoter such that only CD4+ cells express or down-regulate the sarp genes. In this case, an ideal promoter would be the CD4 promoter; however, any suitable CD4+ T cell-specific promoter can be used.

The practice of the present invention employs, unless otherwise indicated, conventional molecular biological techniques, which are within the skill of the art. See e.g., "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

The following examples are provided to illustrate but not limit the present invention.

EXAMPLE 1

Identification and Cloning of the Sarp Family cDNAs

Cells and Tissues

All cell lines were obtained from the American Type Culture Collection (ATCC) and grown and maintained according to the supplier's recommendations.

Tissue specimens for an RNA isolation were taken from male 20 g BALB/c mice (Babko). The primary cardiomyocytes were prepared from hearts of a day-old Sprague Dawley rats according to a technique described by Simpson (1985). The ischemia was performed in a serum and glucose free RPMI media by incubating the cells during 8 hours at 37° C. in an atmosphere of 95% $N_2$/5% $CO_2$. The postischemic reperfusion was stimulated by adding of fetal bovine serum (FBS) to 10%, glucose to 2 g/L and placing the cells in 5% $CO_2$ at 37° C. for 16 hours. For viral infection, the cells were incubated with appropriate amount of the infectious particles in serum free media at 37° C. 2 hour. Then the medium was replaced by the regular growth medium (RPMI/10% FBS). The adenovirus titers were determined by limiting dilution and plaque assay using 293 cells exposed to the virus dilutions. The number of viruses capable to infect 80–90% of cells was determined with the β-galactosidase virus infected cells and X-Gal (5-bromo-4-chloro-3-indolyl β-D-galactoside) staining.

Oligonucleotide Synthesis

Primers for DNA sequencing and PCR, adapters were synthesized on an Applied Biosystems model 394, gel purified and desalted using Sep-Pak C18 cartridges (Water Associates). A 14-mer (5' CCTGTAGATCTCCC 3', SEQ. ID. NO: 15) and an 18-mer (5' ATTTCGGAGATCTACAGG 3', SEQ. ID. NO: 16) oligonucleotides were used with the EcoRI-BgIII adapter. For differential display reactions an arbitrary d(N10) and an anchored oligo(T) such as TTTTTTTTTTTTTTTNS (SEQ. ID. NO: 17) were used.

RNA Isolation

RNA from different cell lines and tissues was isolated using the guanidine-isothiocyanate method of Chomezinski and Sacchi (1987). RNA concentration was determined by spectrophotometry (Sambrook et al., 1989). 20 µg samples of total RNA were subjected to electrophoresis in a 1.2% agarose-formaldehyde gel (Sambrook et al., 1989) and visualized using ethidium bromide. RNA was then transferred using 10×SSC (1×SSC is 0.15M NaCl/0.015M Na-citrate) by diffusion onto a nylon membrane (Hybond N+, Amersham) according to the method of Lichtenstein et al. (1990). Membrane-bound RNA was crosslinked by UV-irradiation as recommended by the manufacturers.

Differential Display

For differential display reactions the first strand cDNA was synthesized using 2 µg of total RNA isolated from either logarithmically growing or quiescent 10T1/2 cells. First strand synthesis was primed using an anchored oligo(dT) with Superscript Reverse Transcriptase (Gibco) according to the manufacturer's protocol. In PCR reactions, arbitrary d(N10) and anchored oligo(dT) primers were used. PCR conditions were essentially the same as published originally in Liang & Pardee, 1992. The PCR-amplified cDNA products were resolved on a 6% DNA sequencing gel (Sambrook et al., 1989). Differentially displayed bands were excised from the gel, reamplified using the same primers and conditions, and inserted into pCRScript (Stratagene).

Construction of the cDNA Library

The mouse 10T1/2 fibroblast λZAP II based cDNA library was constructed essentially as described in (Zapf et al. 1990) with some modifications. Two 40 µl reaction mixtures were prepared containing 10 µg heat denatured poly(A+)RNA, 1×First Strand Buffer (Gibco BRL), 10 mM DTT, 50 units of RNase Block (Stratagene), 2 mM of each dATP, dCTP, dGTP and dTTP, 10 µCi [a-$^{32}$P]dCTP, 400 U Superscript Reverse Transcriptase II (Gibco). 2.5 µg oligo(dT) was added to one reaction mixture and 25 µg d(N6) to the other mixture. Both reaction mixtures were incubated for 1 hour at 42° C. and terminated by heating at 65° C. for 10 min. Second strand synthesis was performed by first adding 362 µL $H_2O$, 80 µL of 5×second strand reaction buffer (100 mM Tris-HCl pH(7.5), 500 mM KCl, 25 mM $MgCl_2$, 50 mM DTT), and 1.5 µL of 15 mg/mL BSA to the first strand reactions. Second strand synthesis was initiated by adding 12 µL of 10 U/µL E. coli DNA polymerase I (NEB) and 2.5 µL of 1 U/µL RNase H (Pharmacia). Reactions were incubated for 1 hour at 15° C., and 1 hour at room temperature. The two reactions, now double stranded cDNA, were combined and ligated to the EcoRI-BgIII adapters (Zapf et al. 1990). Low molecular weight cDNA species and unligated adapters were separated using Bio-Gel A-15 m chromatography (Bio Rad). The ligation of the cDNA to λZAP II/EcoRI/CIAP (Stratagene) was carried out according to the manufacturer's instructions. Packaging and titration were performed essentially following to the supplier's instructions (Stratagene). A library of $8 \times 10^6$ independent recombinant clones was obtained.

Cloning of the Differentially Displaced Gene From Mouse Cells.

To isolate msarp1 cDNA, the quiescent 10T1/2 cell library was screened using the PCR insert as a probe. Approximately $2.5 \times 10^5$ to $3.0 \times 10^5$ recombinant phages were plated in *E. coli* XL-Blue (Stratagene) and, transferred onto nitrocellulose filters (Millipore) according to the manufacturer's instructions. The DNA fragments were $^{32}$P-labeled according to the method described in Feinberg and Vogelstein (1984) *Anal. Biochem.* 137:266–267 and used to screen the library according to the method described in Keifer et al. (1991).

The largest clone, msarp1, was then chosen for further analysis. DNA sequencing of msarp1 was performed by the Sanger & Nicholson dideoxynucleotide method, using M13 forward and internally specific primers.

The msarp1 gene contains a single extended open reading frame encoding a predicted protein product of 295 amino acids (mSARP1), 252 bp of 5'-untranslated sequence and 891 bp of 3'-untranslated sequence with two putative polyadenylation signals positioned 637 bp and 234 bp from the 3'-end. Interestingly the 3'-untranslated region contains eleven conserved 3'-UTR/HMG motifs thought to be involved in postranscriptional degradation of mRNA (Reeves et al., 1987). Global alignment of the msarp1 sequence to Entrez (14.0) using the MacVector package revealed homology to genes encoding for the seven-transmembrane rat proteins homologs of the *Drosophila melanogaster* frizzled (*fz*) gene product.

The msarp1 gene does not have any transmembrane regions, and the C-terminal region is rich in basic amino acids. msarp1 has one hydrophobic stretch, which may represent a signal sequence. Multiple alignments using Entrez and the NCBI gene sequence data banks showed strong homology between the N-terminal region of mSARP1 and the extracellular parts of mouse (FIG. 1B), rat and human genes products. The C-terminal region of mSARP1 contains several short polypeptide stretches which show homology to the sites of frizzled proteins positioned between the transmembrane regions. The EST database revealed a 400 bp DNA sequence isolated from a human breast cDNA library which showed 75% identity to msarp1.

Cloning of Human cDNAs

A human pancreas and human heart cDNA libraries were obtained from Clontech and screened using msarp1 cDNA as a probe. Two cDNA clones, hsarp1 and hsarp3, were recovered from the pancreas library and subjected to further analysis. One clone, hsarp2, was obtained from the human heart cDNA. The hsarp2 cDNA sequence [SEQ ID NO: 18] contains 1302 nucleotides. The full length sequence includes 301 nucleotides of the 5' untranslated region and 62 nucleotides of 3' untranslated region. The hsarp2 cDNA contains one major ORF (hSARP2). The ATG start site is found at position 303, and the termination site is at position 1248. The hsarp2 gene encodes a polypeptide of 314 amino acid residues with an N-terminal methionine and C-terminal lysine. Clone hsarp1 is 890 nucleotides in length and encodes a polypeptide having about 95% homology to msarp1. The ATG of hsarp1 is at position 203 and there is a putative signal peptide recognition site 23 amino acids downstream of the N-terminus. The hsarp3 clone is 1923 nucleotides and encodes a polypeptide 316 amino acids including a putative 28 amino acid secretion signal at the N-terminus.

EXAMPLE 2

Expression of Novel Genes in Tissue Types

Isolated DNA fragments were labeled with [$^{32}$P]dCTP (3000 Ci/mmol, Amersham) in a random priming reaction according to Feinberg and Vogelstein, (1982), supra. Hybridization was carried out according to the standard protocol described in Sambrook et al. (1989), supra. The membranes were washed two times with 2×SSC at room temperature for 30 minutes. Following two additional washes at 56° C. in 0.1×SSC, 0.1% SDS, the membranes were autoradiographed onto a Kodak X-Omat films.

Expression of msarp1 in Mouse Tissue

To analyze msarp1 expression in mouse tissues, Northern blots of various mouse tissues were prepared according to the standard protocol. The results are shown in FIG. 2. High levels of expression were detected in mouse heart and lung. Detectable amounts of transcript were revealed also in kidney. No other mouse tissues expressed the RNA corresponding to msarp1. No expression of msarp1 was detected in transformed cell lines FL5.12; WI-L2; S49; HT29; MCF7.

Expression of the Novel Genes in Human Tissue

Figure 3A:
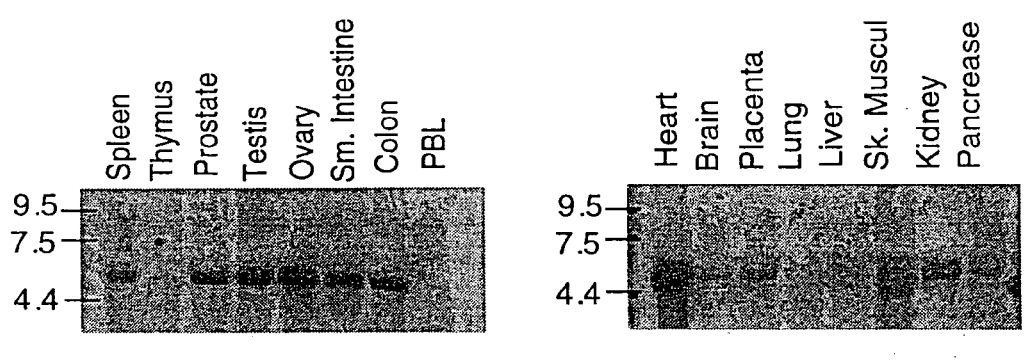
FIG. 3A depicts the results of a Northern blot analysis of multiple human tissues with a probe specific for hsarp2.

To determine expression of the sarp gene family in human tissues, Clontech human multiple tissue Northern blots were probed with labeled hsarp1, hsarp2, and hsarp3, as described above. FIGS. 3A (hsarp2) and 3B (hsarp1 and hsarp3) show the tissue specific expression of hsarp1, hsarp2, and hsarp3.

Figure 3B:
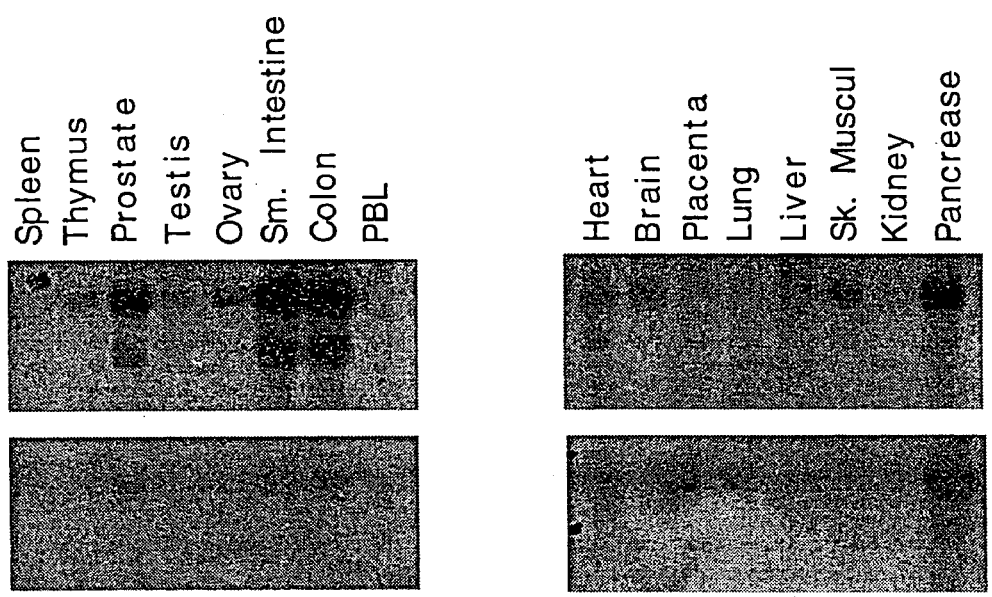
FIG. 3B is a compilation of Northern blots depicting tissue specific expression of hsarp1 and hsarp3 in various human tissues. Multiple tissue northern blots were probed at high stringency conditions.

The results indicate that hsarp2 is expressed in almost all tissue types analyzed (FIG. 3A). Hybridization showed an RNA band sized approximately 5.0 kb. The highest levels of hsarp1 expression were found in pancreas, colon, prostate and small intestine. FIG. 3B. Lower levels of expression were detected in heart, brain, lung, skeletal muscle and prostate. Thymus, spleen, peripheral blood leukocytes, testis, ovary, placenta, liver, kidney and all fetal human tissues have faint or no signals. Hybridization to all tissue types except brain revealed two transcripts of 2.1 kb and 1.6 kb in length, probably reflecting an alternative utilization of the two polyadenylation signals identified in 3'-UTR.

hsarp3 is expressed predominantly in pancreas, and has only one RNA transcript of 2.1 kb in size (FIG. 3B).

Figure 4:
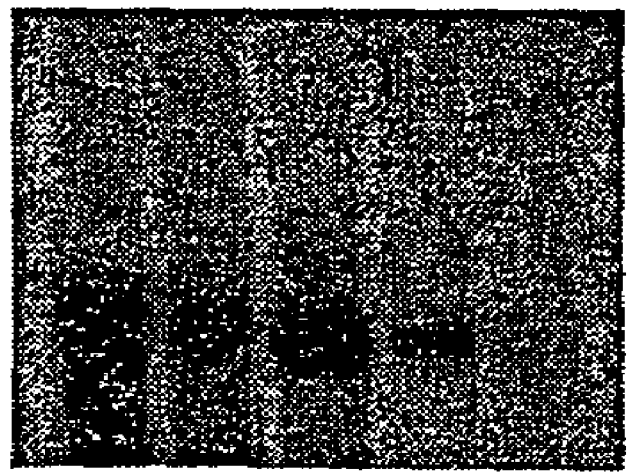
FIG. 4 depicts the results of a Northern blot analysis of normal and transformed cell lines with a probe specific for hsarp2.

Expression of hsarp2 in several transformed and non transformed cell lines was analyzed. No hsarp2 expression was observed in all transformed cell line analyzed. The expression of hsarp2 is detectable in exponentially growing human mammary nontransformed cells and suppressed when the cells reach quiescent conditions (FIG. 4). The same expression pattern of hsarp2 was seen in normal human diploid fibroblast cells.

EXAMPLE 3

Expression of msarp1 in 10T1/2 Cells

To determine differential expression of msarp1, transcription of the gene was evaluated in 10T1/2 cells. Significant induction of msarp1 transcription was seen as the 10T1/2 cells reached quiescence (see FIG. 5). Cells grown to quiescence were reseeded at low density in three plates. At different time points after reseeding, the cells from one of the plates were extracted for RNA isolation, the cells of second plate were used for cell cycle analysis and the third plate of cells deprived of serum for 24 hours to estimate the number of dead cells.

Figure 5:
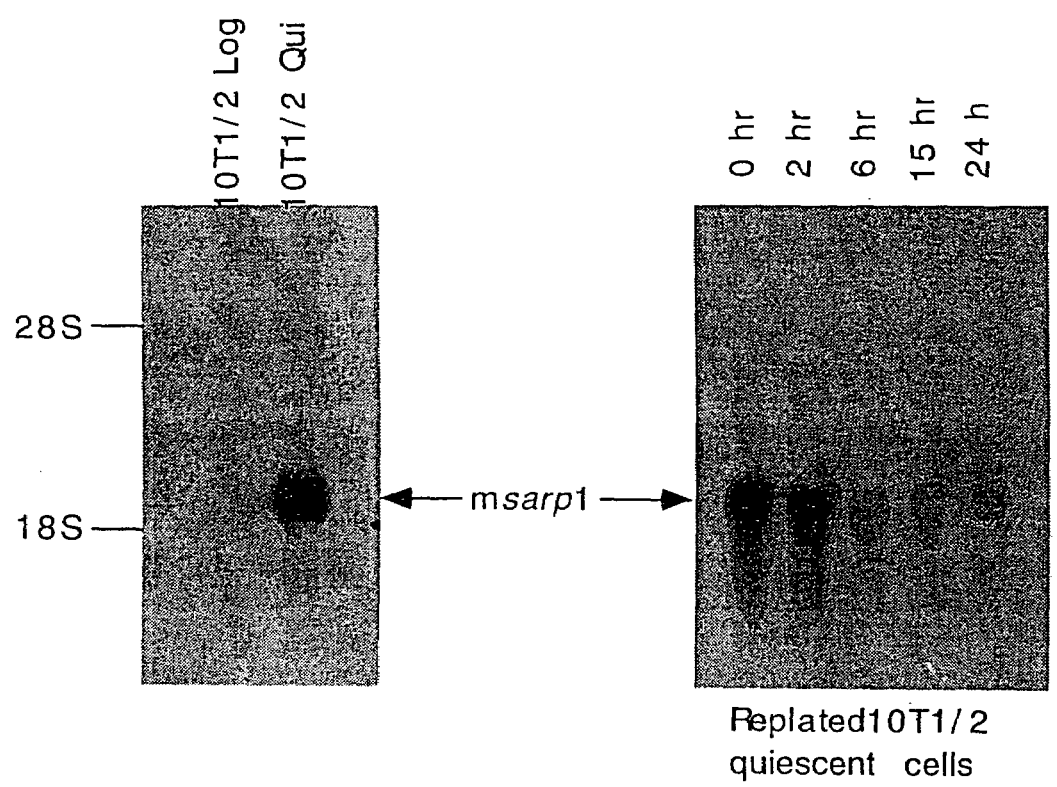
FIG. 5 is a Northern blot depicting expression of msarp1 in 10T1/2 quiescent cells after reseeding at low density.

FIG. 5 represents Northern hybridization of the differentially displayed DNA fragment to the RNA samples isolated from the 10T1/2 cells at different phases of growth: 1–3—exponentially growing, 90 to 95% confluent and quiescent ($G_0$) cells respectively; 4–6—the quiescent cells were replated at lower density and harvested after 0, 2 and 6 hours, respectively. FIG. 5 indicates that the message corresponding to msarp1 disappears shortly after reseeding. Analysis of the second plate indicated that reseeded cells enter the cell cycle 16 hours after reseeding. No significant change in the number of dead cells was observed in the serum-deprived plates. These results suggest in the first 2–3 hours after low density reseeding quiescent cells produce an antiapoptotic factor or factors, in sufficient amounts to maintain typical quiescent cell resistance to serum deprivation.

Since it has previously been shown that media conditioned with exponentially growing 10T1/2 cells also prevents apoptosis, we also analyzed msarp1 expression in serum deprived exponentially growing cells. RNA was isolated at different time points after removal of serum. Hybridization revealed significant induction of the msarp1 message by the 16th hour after serum removal. No induction of msarp1 was observed in cells grown in serum free media supplemented with TPA.

EXAMPLE 4

Expression of msarp1 After Ischemic Injury to Cardiomyocytes

We had previously shown that ischemic injury to myocardial cells triggers apoptosis during reperfusion. Further, we have also shown that the human clone, hsarp1, is expressed in adult heart tissue and not in fetal heart tissue. To determine msarp1 expression relating to ischemic injury and apoptosis, cardiomyocyte cells were subjected to a variety of stressing stimuli. RNA isolated from these cells was electrophoresed and transferred to a membrane for hybridization. Blots probed with msarp1 showed upregulation of msarp1 in all stressed cells. As in the case of human fetal heart tissue, no RNA species corresponding to msarp1 were found in unstressed, primary cardiomyocytes obtained from newborn rats.

EXAMPLE 5 mSARP1 Peptide Interacts with Cell Surface Proteins mSARP1 was stably transfected into MCF7 cells by first introducing a SacI fragment of msarp1 into the EcoRV/NotI sites in pcDNA3. The pcDNA3 construct was then transfected into MCF7 cells using LipofectAMINE reagent (Gibco BRL) according to the manufacturer's instructions.

For indirect immunostaining, trypsinized cells were incubated with rabbit anti-mSARP1 antisera at a 1:100 dilution for 1 hour at 4° C. The cells were washed three times with PBS supplemented with 1% BSA and then incubated with 20 µg/mL FITC-labeled secondary antibodies (Boehringer Mannheim). The cells were analyzed on Becton-Dickinson FACS system, and the resulting data analyzed using CellQuest™ software (Becton Dickinson).

EXAMPLE 6

Apoptotic Effects of hSARP2

Figure 6:
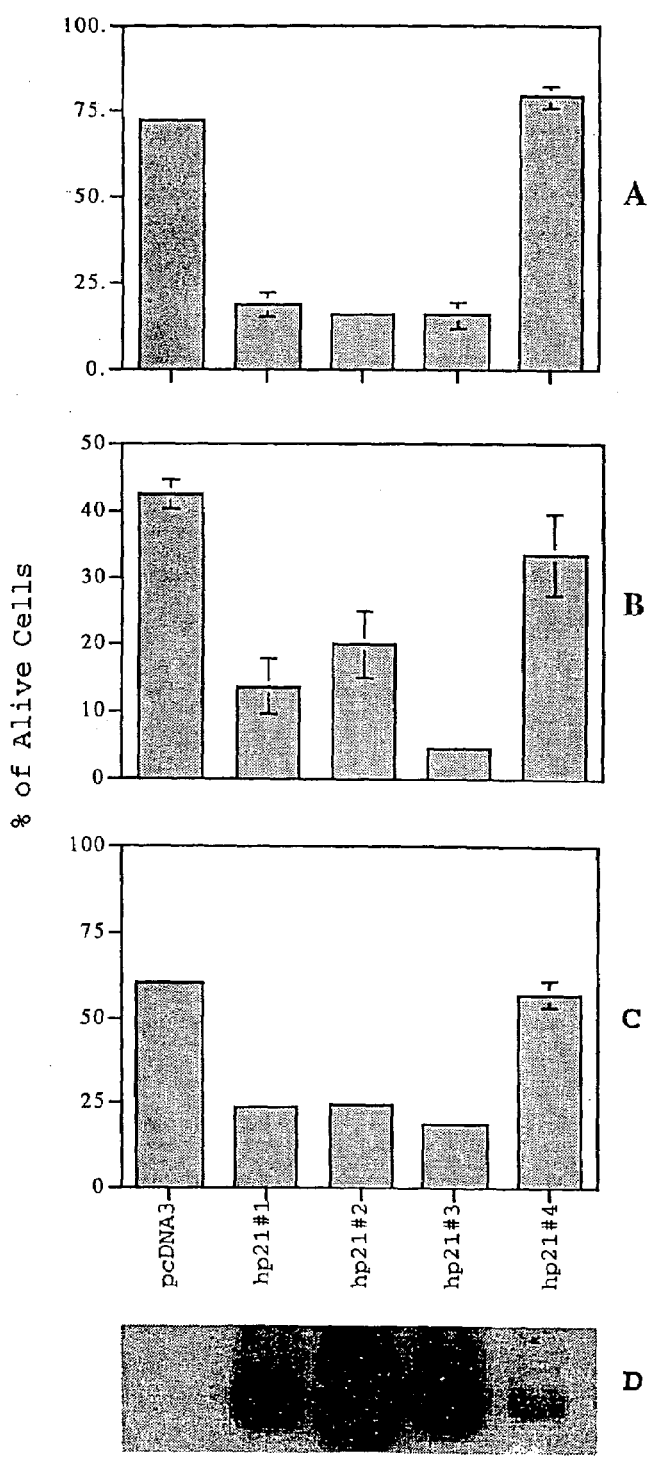
FIG. 6, panels (A) through (C) show the percentage of viable transformed MCF7 cell lines after different treatments. MCF7 cells were transformed with either an expression vector (pcDNA3) or with pcDNA3 carrying the hsarp2 gene. Panel (A) shows the percentage of living cells after seven days of serum deprivation. Panel (B) shows the percentage of living cells after 24 hour treatment with adriamycin at 1 µg/ml. Panel (C) shows the percentage of living cells after 24 hour treatment with hTNF at 50 ng/ml. Panel (D) shows the relative amounts of hsarp2 expression in each of the MCF7 clones used in the experiments described in the Examples presented herein.

The NotI/XbaI fragment of hsarp2 was inserted into the NotI/XbaI sites of the mammalian expression vector pcDNA3 (Invitrogen). MCF7 breast carcinoma cells were transfected with this construct using LipofectAMINE reagent (Gibco BRL) according to manufacturer's protocol. The percentage of living cells was estimated by counting the relative amount of adherent cells using a Coulter Counter (NZ). As shown in FIG. 6, hsarp2 expression causes decrease in the percentage of viable cells. The cells were also treated with hTNF (50 ng/ml) and adriamycin (1 µg/ml). The results obtained are depicted in FIG. 6.

EXAMPLE 7

Effect of mSARP1 on Cardiomyocyte Death

Figure 7:
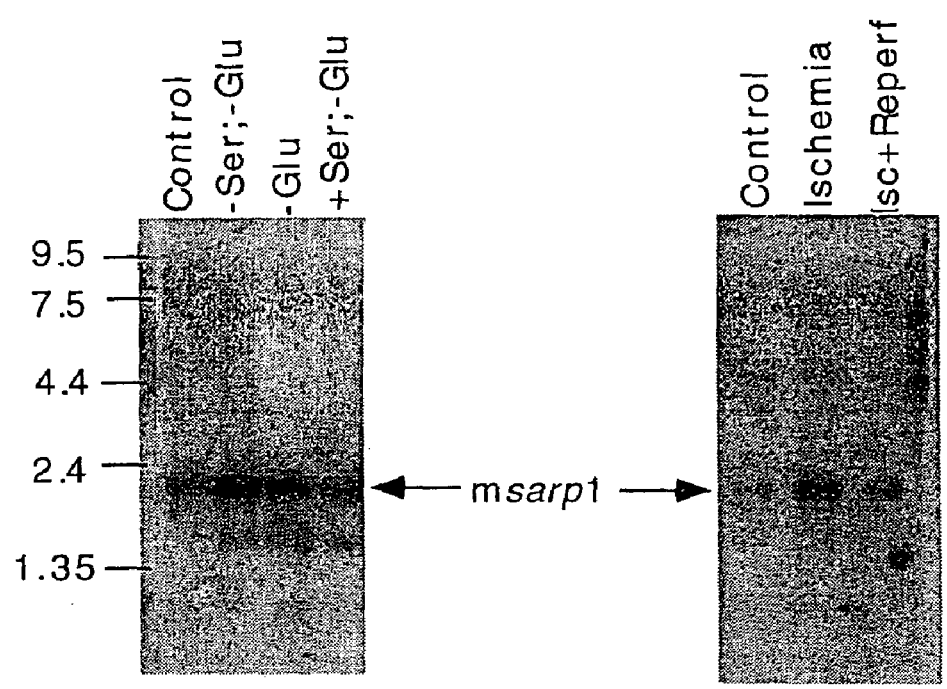
FIG. 7 is a Northern blot of RNA isolated from rat cardiac myocytes after various treatments probed with msarp1 cDNA fragment.

RNA from rat neonatal primary cardiomyocytes was isolated after treatments inducing cell death, such as glucose, serum, or serum and glucose deprivation. Ischemia was simulated by placing the cells in oxygen and growth factor deprived condition for 8 hours followed by 16 hours of incubation in normal environment (referred to as a "reperfusion"). The Northern hybridization presented in FIG. 7 show that sarp1 expression in the cells surviving these treatments is upregulated.

Figure 8:
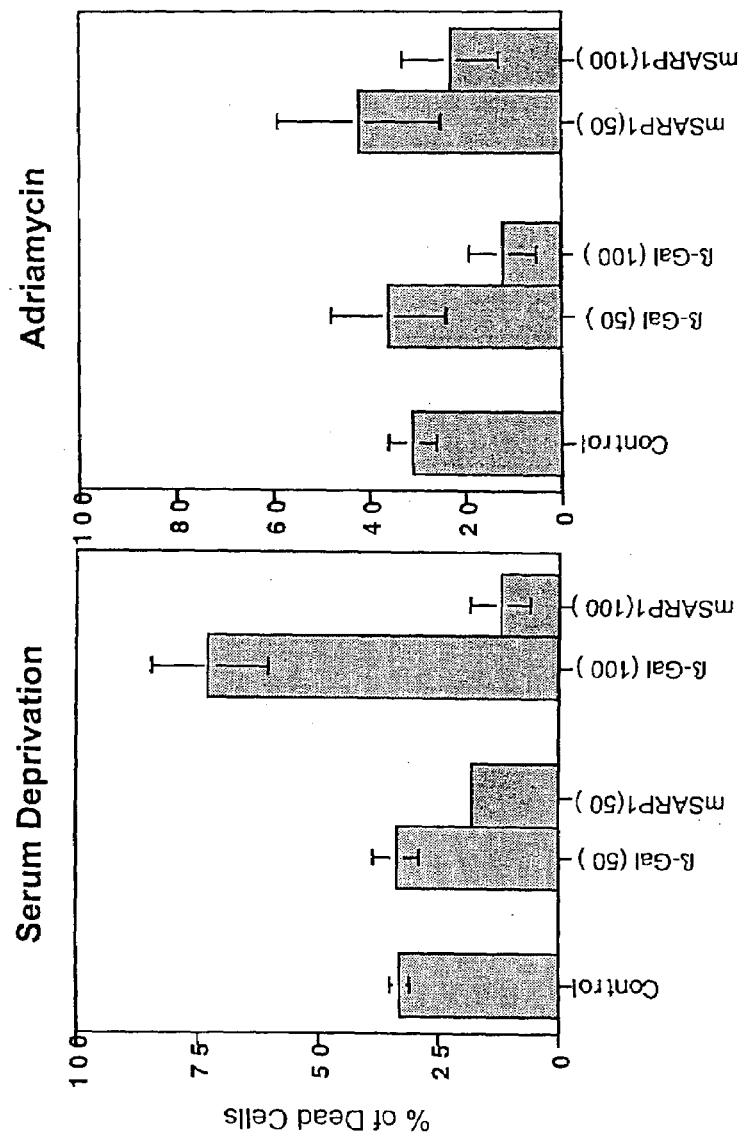
FIG. 8 is 2 bar graphs depicting viability of the control, β-galactosidase, and msarp1 transfected neonatal rat cardiac myocytes subjected for 24 hour to serum free medium or adriamycin treatment. The amount of infections virus particles per cell are shown in parentheses.

In a second experiment, cardiomyocytes plated at high density were infected with recombinant viruses at a multiplicities of 50 and 100 infectious particles per cell. The msarp1 containing recombinant adenovirus was constructed by subcloning of the corresponding cDNA SacI fragment into the NotI/EcoRV site of pAdLXR-1 adenoviral replication-deficient vector. The virus bearing β-galactosidase gene was used as a control. After the infection cells were subjected for 24 hours to serum deprivation or treatment with adriamycin. The cell viability was calculated as a percentage of the adherent cells, in experimental conditions, taken from those of control samples. The results presented in FIG. 8 show that after serum deprivation or adriamycin treatment the amount of viable msarp1-virus infected cells is significantly higher than that for β-galactosidase infected or control, non infected cells.

EXAMPLE 8

Effect of SARP Expression on Apoptosis

C3H/10T1/2 cells were grown in Eagle's basal medium (BME) supplemented with 10% heat-inactivated fetal bovine serum (FBS) at 37° C. in a humidified 5% $CO_2$ atmosphere without antibiotics. Cells were plated at $2 \times 10^3$ cells/mL and fed every 3–4 days. Approximately 2 weeks after the initial seeding, the cells were completely quiescent and few if any mitotic cells were present. To analyze the effect of serum deprivation or cycloheximide treatment, the exponentially proliferating (approximately 75% confluent) or quiescent cultures were transferred to serum-free medium or medium supplemented with 10 µg/mL cycloheximide. At 24 hours, the apoptotic (i.e. non-adherent) cells and the non-apoptotic (i.e. adherent) cells were collected separately and their amounts were evaluated using a cell counter (Coulter Counter ZM). Serum free conditioned medium was obtained after 24 hour incubation of quiescent 10T1/2 cells in BME. The RNA was isolated by the guanidine-isothiocyanate method described in Chomezinski and Sacchi (1987) *Anal. Biochem.* 162:156–59. 20 µg samples of total RNA were subjected to electrophoresis in a 1.2% agarose formaldehyde gel. Sambrook et al. (eds) (1989).

Figure 9:
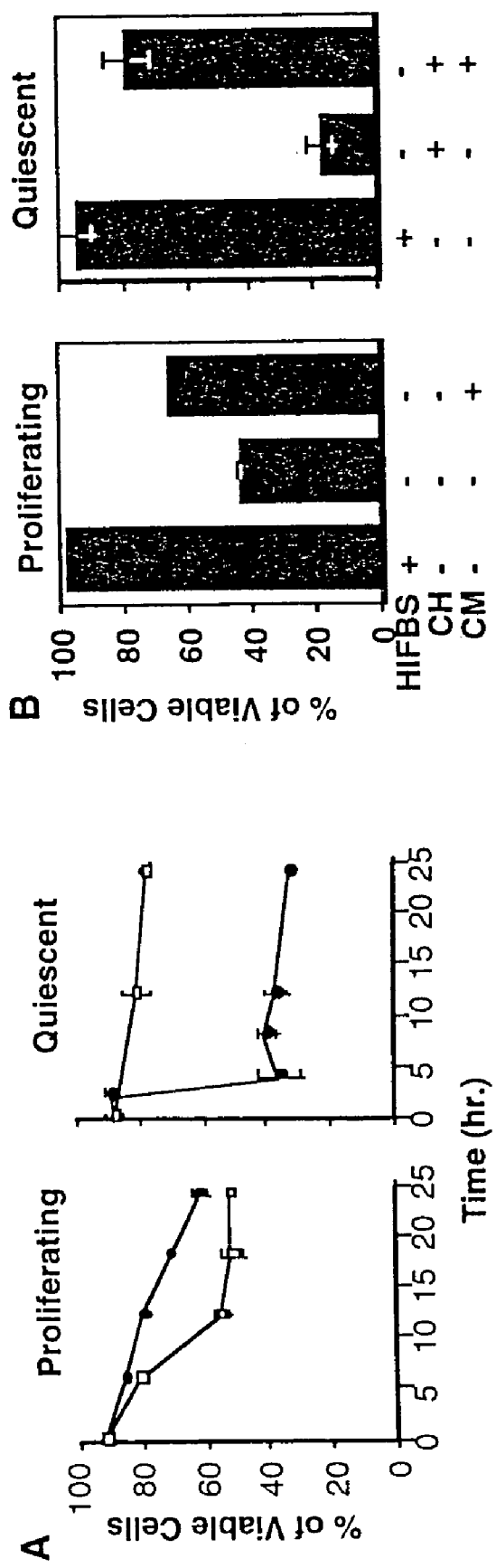
FIG. 9 is a series of graphs depicting (A) the effect of cycloheximide on 10T1/2 log and quiescent cell death induced by serum deprivation and (B) the effect of conditioned medium from quiescent cells on cells subjected to serum deprivation and cycloheximide treatment.

It has previously been shown that exponentially proliferating 10T1/2 cells are especially sensitive to serum deprivation and die by apoptosis. Tomei et al. (1993) *Proc. Natl. Acad Sci. USA* 90:853–857. FIG. 9A shows that after 24 hours in a serum free medium, about 50% of the cells detach and are found to be apoptotic. When cell cultures reach density dependent quiescence, cells become resistant to withdrawal of growth factors and other serum components.

Similarly, quiescent cells are significantly more resistant to the cytotoxic effects of staurosporine, menadione and cis-platinum. These are pro-apoptotic agents that have differing mechanisms of action. During exponential proliferation apoptosis is delayed by the addition of cycloheximide. In contrast, inhibition of protein synthesis rapidly induces death in quiescent cells arrested in $G_0$ (FIG. 9A). Apoptosis of $G_0$ is also induced by puromycin, as well as inhibition of RNA synthesis by actinomycin D or α-amanitin. These results imply that in quiescent 10T1/2 cultures, cells possess all components of the apoptotic pathway but activation is suppressed by quiescent state specific protein(s). This viewpoint is consistent with the observation that conditioned medium from quiescent 10T1/2 cells can inhibit apoptotic death of both serum deprived exponentially growing and cycloheximide treated quiescent 10T1/2 cells (FIG. 9B). These results strongly suggest that the anti-apoptotic protein(s) is secreted from quiescent 10T1/2 cells and influences the response of neighboring cells.

To clone cDNA corresponding to this mRNA species, the 10T1/2 quiescent cells, human heart and pancreas cDNA libraries were screened using the differentially displayed DNA fragment as a probe. Four different recombinants were identified. Two of them screened from 10T1/2 and human pancreas were orthologous and designated as msarp1 and hsarp1. The other two clones hsarp2 and hsarp3, were obtained from the human heart and pancreas libraries, respectively. With the exception of hsarp1, these cDNA clones have a single extended open reading frame predicting full length proteins which share several common structural properties. Starting from the N-terminus, the hydrophobic putative signal peptides are followed by the mature protein sequences, 270–300 amino acids in length with 16 invariant cysteines. Of these, 10 cysteines are located in the N-terminal 110 to 120 amino acids segments which are 25–30% identical to the extracellular cysteine rich domain ("CRD") of frizzled-like proteins. None of the hsarp group contains transmembrane regions which are characteristic of frizzled-like proteins. Wang et al. (1996) *J. Biol. Chem.* 271:4468–4476. The partial polypeptide sequencing of hSARP1 has revealed about 95% identity with the mSARP1.

Figure 10:
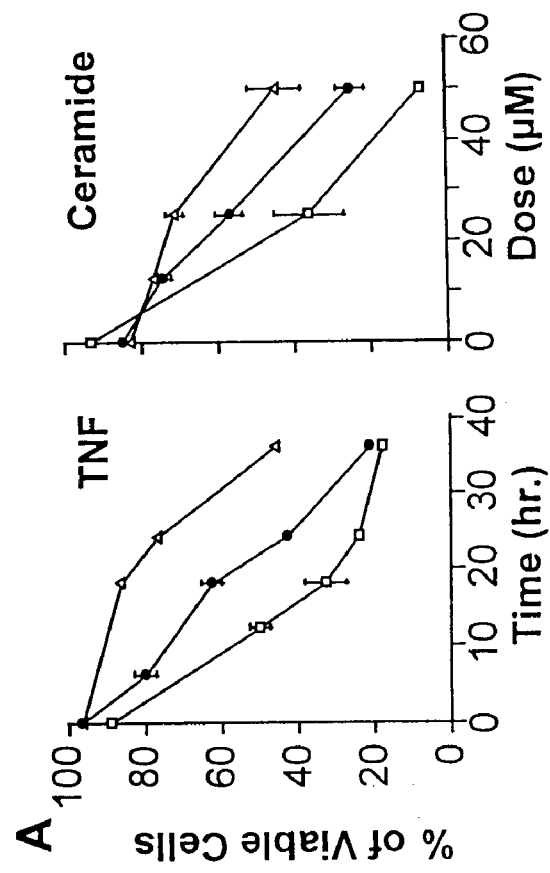
FIG. 10 depicts (A) graphs, (B) a Northern blot, and (C) a Western analysis. The graphs depict the effects of TNF and Ceramide on cell viability in the presence of SARPs. The Northern blot depicts control RNA from cells transfected by pcDNA3, RNA from cells transfected by msarp1 or hsarp2 recombinant vectors. The proteins of serum free conditioned media from 10T1/2 and MCF7 cells were concentrated by filtration and subjected to western analysis using anti-GST-mSARP1 antisera (1:5000 dilution).
Figure 10:
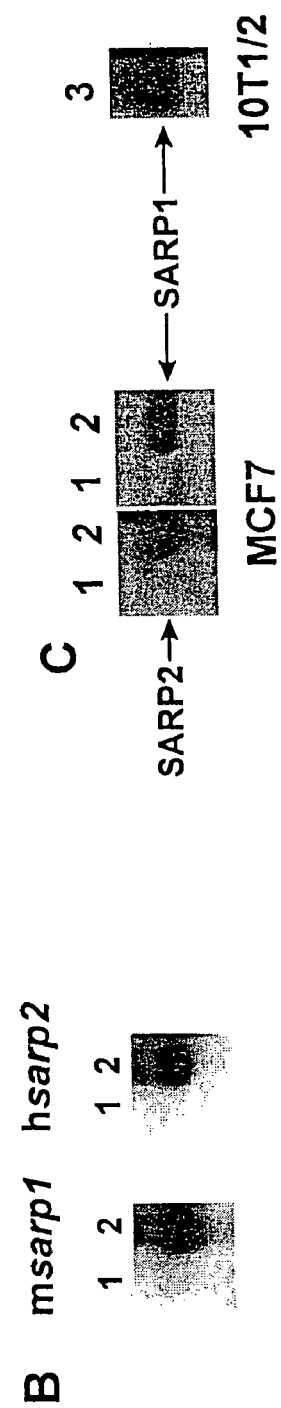

The MCF7 breast adenocarcinoma cell line was chosen as a model to study the involvement of SARP proteins in the processes of apoptosis. The programmed cell death of these cells induced by different agents has been well characterized. Zyed et al. (1994) *Cancer Res.* 54:825–831. This cell type does not express either sarp1 or sarp2. MCF7 cells were stably transfected with a pcDNA3 mammalian expression vector bearing full length msarp1 or hsarp2. The transfectants expressing msarp1 and hsarp2 were selected by Northern hybridization. The growth rate and cell cycle of transfected MCF7 cells were not significantly different from the parental cells; however, the results presented in FIG. 10(A) demonstrate that the expression of mSARP1 and hSARP2 had opposite effects on cell sensitivity to cytotoxic stimuli. The expression of mSARP1 resulted in higher resistance, expression of hSARP2 sensitized the cells to apoptosis induced by TNF and by ceramide, a secondary messenger in apoptotic pathways caused by various agents. Hannun and Obeid (1995) *T. Biochem. Sci.* 20:73–7; and Kolesnick and Fuks (1995) *J. Exp. Med.* 181:1949–52.

Due to the fact that SARPs have the signal sequences but no transmembrane domains, it was believed that they are secreted proteins. This theory was tested as follows. Polyclonal anti-mSARP1 antibodies were raised against the GST-mSARP1 recombinant protein and affinity purified using MBP-mSARP1 affinity column. Bacterial expression of GST-mSARP1 and MBP-mSARP1 fusion proteins was carried out using the pGEX-5X-2 (Pharmacia) and pMAL (NEB) vectors, respectively. For anti-hSARP2 antibodies a polypeptide derived from non-Frizzled-like C-terminal domain (167–185 aa) (SEQ. ID. NO: 19) of the protein was used as an immunogen. Using the resultant affinity purified anti-mSARP1 or anti-hSARP2 antibodies, the secreted proteins were detected in the conditioned media from both the transformed MCF7 cells and untransformed quiescent 10T1/2 (FIG. 10(C)). Notably, the mSARP antibodies fail to interact with hSARP2.

The experiments described identify a new family of genes capable of modulating cellular apoptotic response to cytotoxic signals. It is important to note the high degree of sequence similarity between SARP CRDs and the similar regions of the frizzled proteins, a class of cellular membrane receptors with seven transmembrane domains. In *Drosophila melanogaster,* frizzled proteins are involved in regulation of bristle and hair polarity. Adler (1992) *Cell* 69:1073–1087. Recently, the ability of Dfz2, a frizzled protein family member, to function as a receptor for Wingless protein was reported. Bhanot et al. (1996) *Nature* 382:225–230. Wingless is a member of Wnt gene family whose products are involved in cell-cell and cell-extracellular matrix interaction. Nusse and Varmus (1992) *Cell* 69:1073–1087. Secreted proteins SARPs are involved with regulation of Wnt-frizzled protein interaction. From this viewpoint it is interesting that expression of the members of all three gene families, frizzled, Wnt and sarp, is tissue specific. Wang et al. (1996); Nusse and Varmus (1992); Gavin et al. (1990) *Genes and Devel* 4:2319–2332; and Chan et al. (1992) *J. Biol Chem.* 267:25202–25207. The role of cell-cell and cell-extracellular matrix interaction in regulation of apoptosis is well documented. Rouslahti and Reed (1994) *Cell* 77:477–478; Bates et al. (1994) *Cell. Biol.* 125:403–415; and Boudreau et al. (1995) *Science* 267:891–893. Thus, among other functions all three families of genes are involved in the regulation of programmed cell death.

EXAMPLE 9

Comparison of hsarp Expression in Human Normal and Neoplastic Cells

In this example, human normal and neoplastic tissues were evaluated for their expression of hsarp genes. Normal and neoplastic prostate epithelial tissues were assessed for hsarp1 expression, and normal and neoplastic mammary tissues were assessed for hsarp2 expression.

Experiments were performed as follows: First, digoxigenin (DIG) labeled hsarp RNA probes were obtained using RNA DIG labeling kit (Boerhinger Mannheim GmbH, Concord, Calif.) according to the protocol given in Nonradioactive in Situ Hybridization Application Manual, Second Edition, 1996, p. 44. Then, 5 µm formalin-fixed, paraffin-embedded cancer tissue (prostate epithelial or mammary) sections were hybridized with the appropriate DIG labeled hsarp1 or hsarp2 RNA probe. Finally, detection of mRNA was performed using a Genius kit (Boerhinger Mannheim GmbH, Concord, Calif.) according to the protocol given in Nonradioactive in Situ Hybridization Application Manual, Second Edition, 1996, p. 127.

Figure 11:
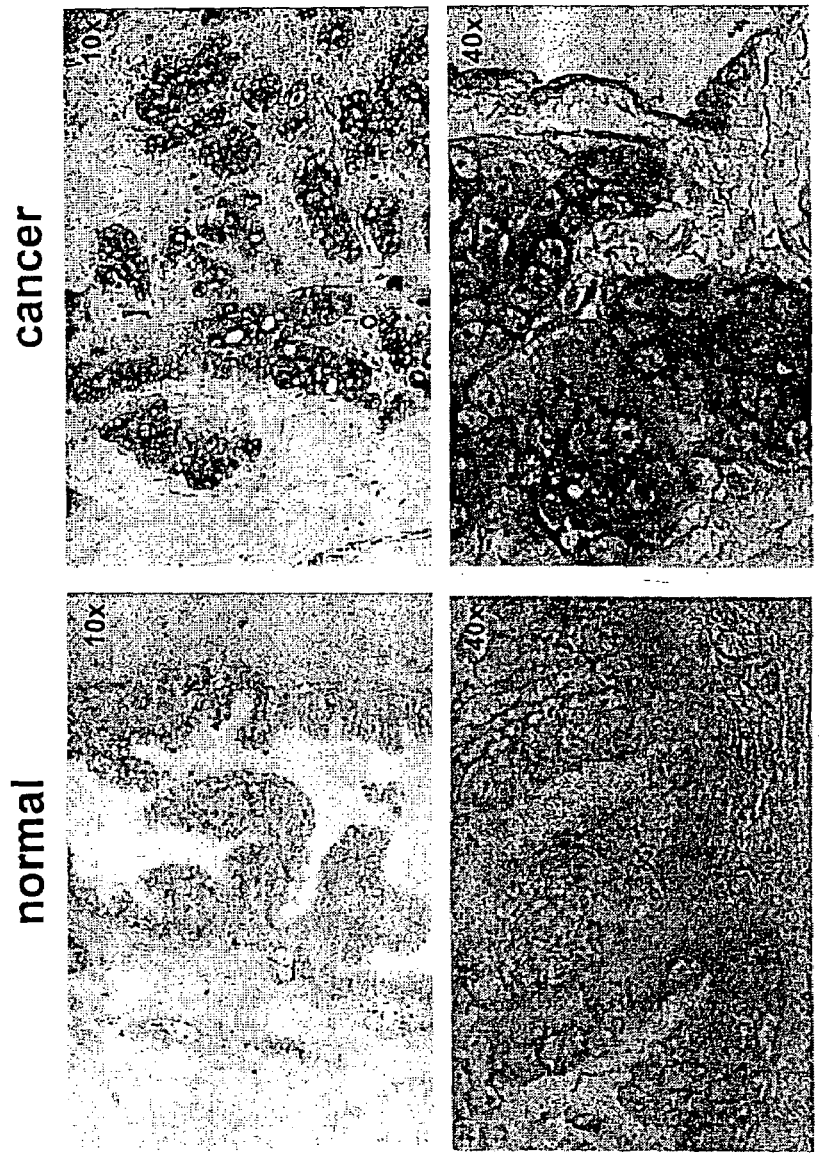
FIG. 11 depicts the comparison of hsarp1 expression in human normal and neoplastic prostate epithelial cells at 10× and 40×magnifications.
Figure 12:
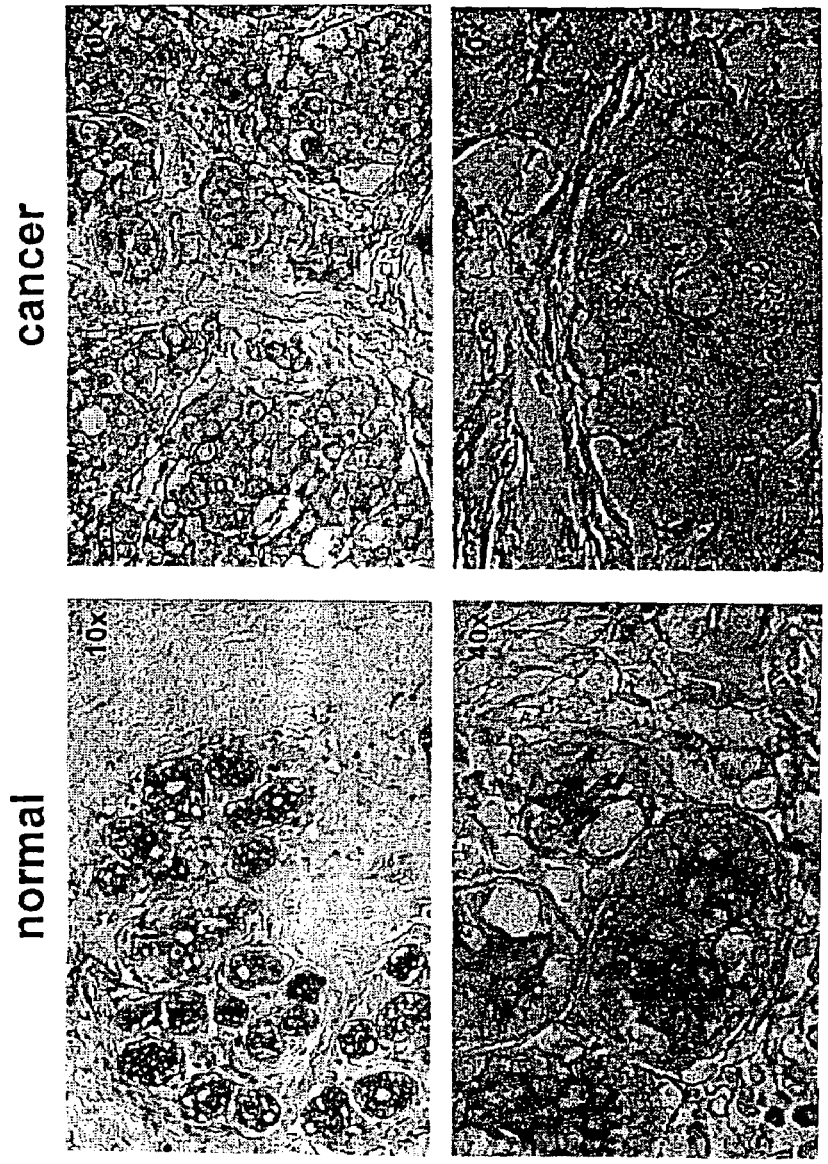
FIG. 12 depicts the comparison of hsarp2 expression in human normal and neoplastic mammary epithelial cells at 10× and 40×magnifications.

FIGS. 11 (prostate epithelial tissue) and 12 (mammary tissue) show the results. Expression of hsarp1 is elevated in prostate tumor cells as compared to the normal tissue control, as evidenced by the pervasive dark area in the 10× and 40× cancer sample as compared to the normal sample. Expression of hsarp2 is suppressed in mammary tumor cells as compared to the normal tissue control. These results support the anti- and pro-apoptotic activity of hSARP1 and hSARP2, respectively. This example shows that detection of sarp gene products in tissues can be used to diagnose a variety of diseases associated with the modulation of hsarp expression, including cancers. Further, because hSARPs are secreted proteins, bodily fluid samples can also be used for such diagnostic purposes.

While this example specifically demonstrates the use of in situ hybridization using an mRNA probe for detection of sarp gene products, alternative methods of detecting the presence of amino acids or nucleic acids in both tissue and bodily fluid are well known in the art. Further, one skilled in these fields is capable of selecting appropriate probes for use in methods of the present invention based on the sequences disclosed herein or incorporated by reference.

EXAMPLE 10

Expression of SARPs Modifies the Intracellular Levels of β-catenin.

In the previous examples, it was shown that the sarp genes encode secreted proteins capable of modifying cell response to pro-apoptotic stimuli. This experiment evaluates the ability of SARP proteins to interfere with the Wnt-frizzled proteins signaling pathway. Recently, it was shown that frizzled proteins function as receptors for members of the Wnt protein family. Yang-Snyder et al. (1996) Curr Biol 6:1302–6; Bhanot et al. (1996) Nature 382:225–30; Orsulic et al. (1996) Current Biology 6:1363–1267; and Perrimon (1996) Cell 86:513–516.

Interaction of Wnt family members with their respective frizzled receptor causes inactivation of glycogen synthase kinase 3β (GSK-3) or its Drosophila homologue Zw-3. Pai et al. (1997) Development 124:2255–66; Cook et al. (1996) EMBO J. 15:4526–4536; and Siegfried et al. (1994) Nature 367:76–80. In the absence of Wnt, GSK-3β phosphorylates β-catenin (Armadillo is its Drosophila homologue). Phosphorylated β-catenin or Armadillo are degraded more rapidly than non-phosphorylated forms of the proteins. Perrimon (1996) Cell 86:513–516; Siegfried et al. (1994) Nature 367:76–80; Rubinfeld et al. (1996) Science 272:1023–6; and Yost et al. (1996) Genes and Development 10:1443–1454. As a result, Wnt signaling causes changes in intracellular concentration of β-catenin or Armadillo and this parameter has been used to register Wnt-frizzled proteins interaction and signal transduction. Bhanot et al. (1996) Nature 382: 225–30. Because SARPs are soluble proteins possessing a domain homologous to CRD of frizzled proteins it was hypothesized that they functioned by interference with Wnt-frizzled protein interaction.

Recently it was shown that β-catenin accumulated in colon cancer (Korinek et al. (1997) Science 275:1784–7; and Morin et al. (1997) Science 275:1787–90); and melanomas (Rubinfeld et al. (1997) Science 275:1790–2), that had mutations in tumor suppressor APC. Moreover regulation of β-catenin is critical to APC's tumor suppressive effect. Morin et al. (1997) Science 275:1787–90. The results herein described show a correlation between the levels of β-catenin and the expression of the SARP family members which possess pro- or anti-apoptotic activity. A higher level of β-catenin in tumors is associated with a reduction in apoptotic cell death, a feature characteristic of carcinogenesis. Thompson (1995) Science 267:1456–1462.

To determine whether SARPs interfered with Wnt-frizzled protein interaction, the expression of β-catenin in MCF7-transfectants was compared. The experiment was performed as follows. Cell Cultures. MCF7 human breast adenocarcinoma cells were plated at $2 \times 10^5$ cells/ml and cultured in Modified Eagle Medium (MEM) supplemented with 10% FBS. Serum free conditioned medium was obtained after 24 hour incubation of quiescent MCF7 cells in MEM.

Transfection of MCF7. MCF7 cells were transfected with the pcDNA3 mammalian expression vector (Invitrogen), containing either no insert, msarp1, or hsarp2 cDNAs, using LipofectAMINE reagent (Gibco) according to manufacturer's protocol. Stable transfectants and two-three weeks later single cell originated clones were selected with 1 mg/ml G418 and expression of the respective genes was confirmed by Northern hybridization.

Immunohistochemistry. Paraformaldehyde-fixed transfected MCF7 cells grown on 4-well Lab-Tek chamber slides were probed by anti-β-catenin monoclonal IgG (Transduction Laboratories). Staining was performed by avidin-biotin-peroxydase system (Vector Laboratories) using diaminobenzidine as a substrate. IgG isolated from preimmune serum was used as a negative control.

Western Immunoblot. For Western analysis the samples of conditioned media were concentrated using CENTRIPREP-10 concentrators (AMICON). Cells were harvested in extraction buffer consisting of 20 mM tris-HCl (pH 7.8), 5 mM $MgCl_2$, 250 mM sucrose, 1% NP40. After 1 hour incubation on ice extracts were clarified by centrifugation. Protein concentrations of the cellular extracts were determined using DC Protein Assay kit (Bio Rad). Equal amount of proteins were subjected to SDS/PAGE (Sambrook, J., et al. (1989) Molecular Cloning: A Laboratory Manual (Second ed.) (CSHL Press), transferred onto nitrocellulose membranes and probed with the anti-GST-mSARP1 polyclonal affinity purified IgG (1 µg/mL) or anti-β-catenin monoclonal IgG (Transduction Laboratories).

Figure 13:
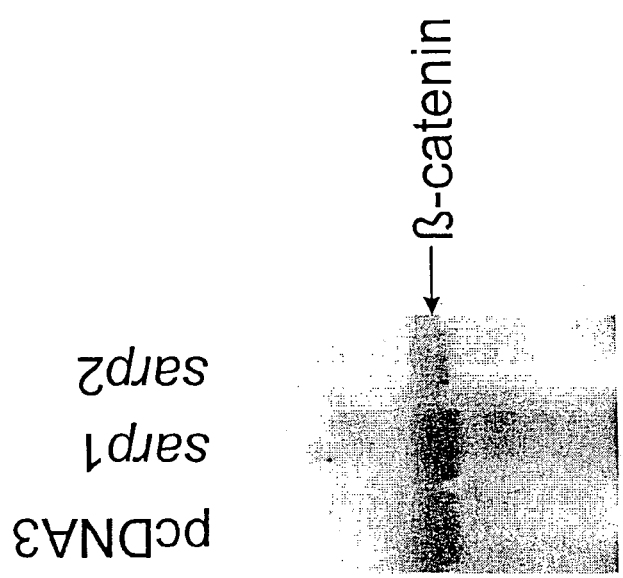
FIG. 13 depicts the detection by Western analysis of β-catenin in MCF7 cells transfected with pcDNA3, msarp1 and hsarp2.

The results appear in FIG. 13, an image of a Western immunoblot which shows that expression of SARP2 decreases the intracellular concentration of β-catenin. The effect of SARP1 on the levels of β-catenin is more complicated. Western blot was not sensitive enough to discern a significant difference between SARP1 and the control, but immunohistochemical data revealed a higher concentration of β-catenin in the SARP1 transfectants. It is clear from these results that the expression of SARPs modifies the intracellular levels of β-catenin, supporting that SARPs interfere with Wnt-frizzled proteins signaling pathway.

This example supports that sarp genes and their products can be used not only to diagnose a variety of diseases associated with the modulation of hsarp expression, including cancers, but also to actively interfere with the action of these diseases on an intracellular level, and therefor to treat these diseases.

Further, the present invention encompasses methods of screening for potential therapeutic agents that modulate the interaction between SARP and Wnt-frizzled proteins by comparing the effect of SARPs on the Wnt-frizzled signaling pathway in the presence or absence of the therapeutic agent in question. Generally, such a drug screening assay can be performed by (a) combining a Wnt protein and a SARP protein under conditions in which they interact, to form a test sample; (b) exposing said test sample to a potential therapeutic agent and; (c) monitoring the interaction of the SARP protein and the frizzled protein; wherein, a potential therapeutic agent is selected for further study when it modifies the interaction compared to a control test sample to which no potential therapeutic agent has been added.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

What is claimed is:

1. An isolated polypeptide comprising the amino acid sequence of SEQ ID NO:7.

2. The polypeptide of claim 1, wherein said polypeptide consists of a fragment of SEQ ID NO:7, said fragment comprising at last 15 contiguous amino acid residues of SEQ ID NO:7.

3. An isolated polypeptide consisting of a fragment of SEQ ID NO:7, said fragment comprising at last 10 contiguous amino acid residues of SEQ ID NO:7.

4. An isolated polypeptide encoded by a sequence chosen from:

a) a polynucleotide comprising the nucleic acid sequence of SEQ ID NO:18;
   b) a polynucleotide fragment of SEQ ID NO:18 consisting of at least 30 contiguous nucleotides of the coding region of SEQ ID NO:18; and
   c) a polynucleotide consisting of a nucleic acid sequence that is fully complementary to a nucleic acid sequence of (a) or (b).

5. The polypeptide of claim 4, wherein said polypeptide consist of a fragment of the amino acid sequence encoded by SEQ ID NO:18, said fragment comprising at least 10 contiguous amino acids of said amino acid sequence.

6. The polypeptide of claim 4, wherein said polypeptide consist of a fragment of the amino acid sequence encoded by SEQ ID NO:18, said fragment comprising at least 15 contiguous amino acids of said amino acid sequence.

7. The polypeptide of claim 4, wherein said polypeptide consist of an amino acid sequence encoded by a nucleic acid sequence consisting of a fragment of the coding region of SEQ ID NO:18, said fragment comprising at least 500 contiguous nucleotides of the coding region of SEQ ID NO:18.

* * * * *

UNITED STATES PATENT AND TRADEMARK OFFICE
CERTIFICATE OF CORRECTION

| | |
|---|---|
| PATENT NO. | : 7,045,596 B2 |
| APPLICATION NO. | : 10/146474 |
| DATED | : May 16, 2006 |
| INVENTOR(S) | : Umansky et al. |

Page 1 of 1

It is certified that error appears in the above-identified patent and that said Letters Patent is hereby corrected as shown below:

At column 69, line 17, delete "last" and insert -- least -- therein.

At column 69, line 20, delete "last" and insert -- least -- therein.

At column 70, line 16, delete "consist" and insert -- consists -- therein.

At column 70, line 20, delete "consist" and insert -- consists -- therein.

At column 70, line 24, delete "consist" and insert -- consists -- therein.

Signed and Sealed this

Ninth Day of January, 2007

JON W. DUDAS
*Director of the United States Patent and Trademark Office*